US007059993B2

(12) United States Patent
Ding et al.

(10) Patent No.: US 7,059,993 B2
(45) Date of Patent: *Jun. 13, 2006

(54) **THERMAL TOLERANT CELLULASE FROM *ACIDOTHERMUS CELLULOLYTICUS***

(75) Inventors: Shi-You Ding, Golden, CO (US); William S. Adney, Golden, CO (US); Todd B. Vinzant, Golden, CO (US); Michael E. Himmel, Littleton, CO (US); Stephen R. Decker, Berthoud, CO (US)

(73) Assignee: Midwest Research Institute, Kansas City, MO (US)

( * ) Notice: Subject to any disclaimer, the term of this patent is extended or adjusted under 35 U.S.C. 154(b) by 102 days.

This patent is subject to a terminal disclaimer.

(21) Appl. No.: 09/917,383

(22) Filed: Jul. 28, 2001

(65) Prior Publication Data

US 2003/0104522 A1   Jun. 5, 2003

(51) Int. Cl.
*C12N 9/42* (2006.01)
(52) U.S. Cl. .................................................. 475/209
(58) Field of Classification Search ................ 435/209, 435/69.7
See application file for complete search history.

(56) References Cited

U.S. PATENT DOCUMENTS

| | | | |
|---|---|---|---|
| 5,110,735 A | 5/1992 | Tucker et al. ................ | 435/208 |
| 5,366,884 A | 11/1994 | Adney et al. ................ | 435/204 |
| 5,432,075 A | 7/1995 | Himmel et al. .............. | 435/204 |
| 5,514,584 A | 5/1996 | Lastick et al. ............ | 435/252.3 |
| 5,536,655 A | 7/1996 | Thomas et al. .............. | 435/204 |
| 5,712,142 A | 1/1998 | Adney et al. ................ | 435/204 |
| 6,013,860 A | 1/2000 | Himmel et al. .............. | 800/278 |
| 6,126,698 A | 10/2000 | Liu et al. ........................ | 8/401 |

OTHER PUBLICATIONS

Sakon, J., et al. (1996) Biochemistry 35, 10648-10660.*
Al-Sulami, A. A., et al. "Purification and Properties of Cellulases from a Local Isolate of *Cellulomonas flavigena*."Dirasat, vol. 19B, No. 4 (1992), pp 139-55 (Univ.Jordan)..
Baker, J. O., et al. "Synergism Between Purified Bacterial and Fungal Cellulases." *Enzymatic Degredation of Insoluble Carbohydrates,* Am. Chem. Society Symp. Ser. vol. 618 (1995) pp 113-41.
PCT International Search Report, PCT/US01/23817, Apr. 22, 2002.
Meinke A. et al., "Cellobiohydrolase A (CbhA) from the cellulytic bacterium Cellulomonas fini is a beta-1, 4-exocellobiohydrolase analogous to Trichoderma reesei CBH II." Molecular Microbiology, vol. 12, No. 3, 1994, pp. 413-422, XP008002307.
Sunna A. et al., "A novel thermostable multidomain 1, 4-beta-xylanase from 'Caldibacillus cellulovorans' and effects of its xylan-binding comain on enzyme activity." Microbiology, vol. 146, No. 11, Nov. 2000, pp. 2000, pp. 2947-2955, XP008002301.
WO 00/14208 A, (Genecor International) Mar. 16, 2000.
WO 00/70031 A, (Adney, William S. et al.) Nov. 23, 2000.
WO 96/02551 A, (Midwest Research Institute) Feb. 1, 1996.

* cited by examiner

*Primary Examiner*—Charles L. Patterson, Jr.
(74) *Attorney, Agent, or Firm*—Paul J. White

(57) ABSTRACT

The invention provides a thermal tolerant cellulase that is a member of the glycoside hydrolase family. The invention further discloses this cellulase as GuxA. GuxA has been isolated and characterized from *Acidothermus cellulolyticus*. The invention further provides recombinant forms of the identified GuxA. Methods of making and using GuxA polypeptides, including fusions, variants, and derivatives, are also disclosed.

57 Claims, 2 Drawing Sheets

FIG. 2

Diversity of glycoside hydrolase families

| Glycoside Hydrolase Families | 1 | 2 | 3 | 5 | 6 | 7 | 8 | 9 | 10 | 11 | 12 | 13 | 15 | 16 | 18 | 24 | 27 | 28 | 31 | 32 | 35 | 36 | 43 | 44 | 45 | 47 | 48 | 49 | 51 | 54 | 61 | 62 | 67 | 74 |
|---|---|---|---|---|---|---|---|---|---|---|---|---|---|---|---|---|---|---|---|---|---|---|---|---|---|---|---|---|---|---|---|---|---|---|
| Aspergillus niger | 1 | 1 | 1 | 2 | 1 | 2 | 2 |  |  | 5 | 1 | 1 | 1 | 1 |  |  | 2 | 8 | 1 | 4 | 1 | 1 | 1 |  |  | 1 |  | 1 | 2 | 3 |  | 1 | 1 |  |
| Trichoderma reesei | 1 |  | 2 | 2 |  | 1 | 2 |  | 1 |  | 2 |  | 1 | 1 |  | 2 |  |  |  |  |  | 1 |  |  | 1 |  |  |  |  | 1 |  |  | 1 |  |
| Clostridium thermocellum | 1 |  | 1 | 6 |  |  | 1 | 8 | 3 | 2 |  |  |  |  | 3 | 1 | 3 |  |  |  |  |  |  | 1 |  | 1 | 1 |  |  |  |  |  |  |  |
| Thermobifida fusca | 1 |  |  |  | 2 | 2 |  |  | 2 |  | 1 |  |  |  |  |  |  |  |  |  |  |  |  |  |  |  | 1 |  |  |  |  |  |  |  |
| Cellulomonas fimi | 1 | 1 |  | 1 | 2 |  |  |  | 2 | 2 | 1 |  |  |  |  | 1 |  |  |  |  |  |  |  |  |  |  | 1 |  |  |  | 1 |  |  |  |
| Acidothermus cellulolyticus |  |  |  | 2 | 1 |  |  |  |  |  | 1 |  |  |  |  |  |  |  |  |  |  |  |  |  |  |  | 1 |  |  |  |  |  |  | 1 |

THERMAL TOLERANT CELLULASE FROM *ACIDOTHERMUS CELLULOLYTICUS*

GOVERNMENT INTERESTS

The United States Government has rights in this invention under Contract No. DE-AC36-99GO10337 between the United States Department of Energy and the National Renewable Energy Laboratory, a Division of the Midwest Research Institute.

FIELD OF THE INVENTION

The invention generally relates to a novel cellulase from Acidothermus cellulolyticus, GuxA. More specifically, the invention relates to purified and isolated GuxA polypeptides, nucleic acid molecules encoding the polypeptides, and processes for production and use of GuxA, as well as variants and derivatives thereof.

BACKGROUND OF THE INVENTION

Plant biomass as a source of energy production can include agricultural and forestry products, associated by-products and waste, municipal solid waste, and industrial waste. In addition, over 50 million acres in the United States are currently available for biomass production, and there are a number of terrestrial and aquatic crops grown solely as a source for biomass (A Wiselogel, et al. Biomass feedstocks resources and composition. In C E Wyman, ed. Handbook on Bioethanol: Production and Utilization. Washington, DC: Taylor & Francis, 1996, pp 105–118). Biofuels produced from biomass include ethanol, methanol, biodiesel, and additives for reformulated gasoline. Biofuels are desirable because they add little, if any, net carbon dioxide to the atmosphere and because they greatly reduce ozone formation and carbon monoxide emissions as compared to the environmental output of conventional fuels. (P Bergeron. Environmental impacts of bioethanol. In C E Wyman, ed. Handbook on Bioethanol: Production and Utilization. Washington, DC: Taylor & Francis, 1996, pp 90–103).

Plant biomass is the most abundant source of carbohydrate in the world due to the lignocellulosic materials composing the cell walls of all higher plants. Plant cell walls are divided into two sections, the primary and the secondary cell walls. The primary cell wall, which provides structure for expanding cells (and hence changes as the cell grows), is composed of three major polysaccharides and one group of glycoproteins. The predominant polysaccharide, and most abundant source of carbohydrates, is cellulose, while hemicellulose and pectin are also found in abundance. Cellulose is a linear beta-(1,4)-D-glucan and comprises 20% to 30% of the primary cell wall by weight. The secondary cell wall, which is produced after the cell has completed growing, also contains polysaccharides and is strengthened through polymeric lignin covalently cross-linked to hemicellulose.

Carbohydrates, and cellulose in particular, can be converted to sugars by well-known methods including acid and enzymatic hydrolysis. Enzymatic hydrolysis of cellulose requires the processing of biomass to reduce size and facilitate subsequent handling. Mild acid treatment is then used to hydrolyze part or all of the hemicellulose content of the feedstock. Finally, cellulose is converted to ethanol through the concerted action of cellulases and saccharolytic fermentation (simultaneous saccharification fermentation (SSF)). The SSF process, using the yeast Saccharomyces cerevisiae for example, is often incomplete, as it does not utilize the entire sugar content of the plant biomass, namely the hemicellulose fraction.

The cost of producing ethanol from biomass can be divided into three areas of expenditure: pretreatment costs, fermentation costs, and other costs. Pretreatment costs include biomass milling, pretreatment reagents, equipment maintenance, power and water, and waste neutralization and disposal. The fermentation costs can include enzymes, nutrient supplements, yeast, maintenance and scale-up, and waste disposal. Other costs include biomass purchase, transportation and storage, plant labor, plant utilities, ethanol distillation, and administration (which may include technology-use licenses). One of the major expenses incurred in SSF is the cost of the enzymes, as about one kilogram of cellulase is required to fully digest 50 kilograms of cellulose. Economical production of cellulase is also compounded by factors such as the relatively slow growth rates of cellulase-producing organisms, levels of cellulase expression, and the tendency of enzyme-dependent processes to partially or completely inactivate enzymes due to conditions such as elevated temperature, acidity, proteolytic degradation, and solvent degradation.

Enzymatic degradation of cellulose requires the coordinate action of at least three different types of cellulases. Such enzymes are given an Enzyme Commission (EC) designation according to the Nomenclature Committee of the International Union of Biochemistry and Molecular Biology (Eur. J. Biochem. 264: 607–609 and 610–650, 1999). Endo-beta-(1,4)-glucanases (EC 3.2.1.4) cleave the cellulose strand randomly along its length, thus generating new chain ends. Exo- beta-(1,4)-glucanases (EC 3.2.1.91) are processive enzymes and cleave cellobiosyl units (beta-(1,4)-glucose dimers) from free ends of cellulose strands. Lastly, beta-D-glucosidases (cellobiases: EC 3.2.1.21) hydrolyze cellobiose to glucose. All three of these general activities are required for efficient and complete hydrolysis of a polymer such as cellulose to a subunit, such as the simple sugar, glucose.

Highly thermostable enzymes have been isolated from the cellulolytic thermophile *Acidothermus cellulolyticus* gen. nov., sp. nov., a bacterium originally isolated from decaying wood in an acidic, thermal pool at Yellowstone National Park. A. Mohagheghi et al., (1986) *Int. J. Systematic Bacteriology*, 36(3): 435–443. One cellulase enzyme produced by this organism, the endoglucanase EI, is known to display maximal activity at 75° C. to 83° C. M. P. Tucker et al. (1989), Bio/Technology, 7(8): 817–820. E1 endoglucanase has been described in U.S. Pat. No. 5,275,944. The *A. cellulolyticus* E1 endoglucanase is an active cellulase; in combination with the exocellulase CBH I from *Trichoderma reesei*, E1 gives a high level of saccharification and contributes to a degree of synergism. Baker J O et al. (1994), *Appl. Biochem. Biotechnol.*, 45/46: 245–256. The gene coding E1 catalytic and cellulose binding domains and linker peptide were described in U.S. Pat. No. 5,536,655. E1 has also been expressed as a stable, active enzyme from a wide variety of hosts, including *E. coli, Streptomyces lividans, Pichia pastoris*, cotton, tobacco, and Arabidopsis (Dai Z, Hooker B S, Anderson D B, Thomas S R. Transgenic Res. Feb. 9, 2000; (1):43–54).

There is a need within the art to generate alternative cellulase enzymes capable of assisting in the commercial-scale processing of cellulose to sugar for use in biofuel production. Against this backdrop the present invention has been developed.

The potential exists for the successful, commercial-scale expression of heterologous cellulase polypeptides, and in particular novel cellulase polypeptides with or without any one or more desirable properties such as thermal tolerance, and partial or complete resistance to extreme pH inactivation, proteolytic inactivation, solvent inactivation, chaotropic agent inactivation, oxidizing agent inactivation, and detergent inactivation. Such expression can occur in fungi, bacteria, and other hosts.

SUMMARY OF THE INVENTION

The present invention provides GuxA, a novel member of the glycoside hydrolase (GH) family of enzymes, and in particular a thermal tolerant glycoside hydrolase useful in the degradation of cellulose. GuxA polypeptides of the invention include those having an amino acid sequence shown in SEQ ID NO:1, as well as polypeptides having substantial amino acid sequence identity to the amino acid sequence of SEQ ID NO:1 and useful fragments thereof, including, a first catalytic domain having significant sequence similarity to the GH6 family, a second catalytic domain having significant sequence similarity to the GH12 family, a first cellulose binding domain (type II) and a second cellulose binding domain (type III).

The invention also provides a polynucleotide molecule encoding GuxA polypeptides and fragments of GuxA polypeptides, for example catalytic and cellulose binding domains. Polynucleotide molecules of the invention include those molecules having a nucleic acid sequence as shown in SEQ ID NO:2; those that hybridize to the nucleic acid sequence of SEQ ID NO:2 under high stringency conditions; and those having substantial nucleic acid identity with the nucleic acid sequence of SEQ ID NO:2.

The invention includes variants and derivatives of the GuxA polypeptides, including fusion proteins. For example, fusion proteins of the invention include GuxA polypeptide fused to a heterologous protein or peptide that confers a desired function. The heterologous protein or peptide can facilitate purification, oligomerization, stabilization, or secretion of the GuxA polypeptide, for example. As further examples, the heterologous polypeptide can provide enhanced activity, including catalytic or binding activity, for GuxA polypeptides, where the enhancement is either additive or synergistic. A fusion protein of an embodiment of the invention can be produced, for example, from an expression construct containing a polynucleotide molecule encoding GuxA polypeptide in frame with a polynucleotide molecule for the heterologous protein. Embodiments of the invention also comprise vectors, plasmids, expression systems, host cells, and the like, containing a GuxA polynucleotide molecule. Genetic engineering methods for the production of GuxA polypeptides of embodiments of the invention include expression of a polynucleotide molecule in cell free expression systems and in cellular hosts, according to known methods.

The invention further includes compositions containing a substantially purified GuxA polypeptide of the invention and a carrier. Such compositions are administered to a biomass containing cellulose for the reduction or degradation of the cellulose.

The invention also provides reagents, compositions, and methods that are useful for analysis of GuxA activity.

These and various other features as well as advantages which characterize the present invention will be apparent from a reading of the following detailed description and a review of the associated drawings.

The following Tables 5 and 6 includes sequences used in describing embodiments of the present invention. In Table 5, the abbreviations are as follows: CD, catalytic domain; CBD_II carbohydrate binding domain type II; CBD_III, carbohydrate binding domain type III; and FN-III, fibronectin domain type III. When used herein, N* indicates a string of unknown nucleic acid units, and X* indicates a string of unknown amino acid units, for example about 50 or more. Table 5 includes approximate start and stop information for segments, and Table 6 includes amino acid sequence data for segments.

TABLE 5

Nucleotide and polypeptide segments.

| GuxA Segment | base BEGIN | base END | Length, bp | aa BEGIN No. | aa | aa END No. | aa | Length, aa | SEQ ID No. (amino acid) | SEQ ID No. (nucleotide) |
|---|---|---|---|---|---|---|---|---|---|---|
| Total length | 1 | 3687 | 3687 | 1 | M | 1228 | S | 1228 | 1 | 2 |
| Signal (potential) | 1 | 159 | 159 | 1 | M | 53 | A | 53 | 3 | |
| CD (GH6) | 160 | 1428 | 1269 | 54 | A | 476 | V | 423 | 4 | |
| CBD III | 1750 | 2199 | 450 | 584 | V | 733 | E | 150 | 5 | |
| FN-III | 2266 | 2520 | 255 | 756 | D | 840 | V | 85 | 6 | |
| CD (GH12) | 2578 | 3270 | 693 | 860 | D | 1090 | G | 231 | 7 | |
| CBD II | 3382 | 3684 | 303 | 1128 | G | 1228 | S | 101 | 8 | |

TABLE 6

Gene/polypeptide segments with amino acid sequences.

| SEQ ID No. (amino acid) | SEQ ID No. (nucleotide) | GuxA Segment | segment data |
|---|---|---|---|
| 1 | 2 | Total length | SEQ ID NO: 1 (see Table 1); SEQ ID NO: 2 (see Table 2) |

TABLE 6-continued

Gene/polypeptide segments with amino acid sequences.

| SEQ ID No. (amino acid) | SEQ ID No. (nucleotide) | GuxA Segment | segment data |
|---|---|---|---|
| 3 | | Signal (potential) | MERTQQSGRNCRYQRGTTRMPAISKRLRAGVLAGAVSIAASIVPLAMQHPAIA |
| 4 | | CD (GH6) | ATHVDNPYAGATFFVNPYWAQEVQSEAANQTNATLAAKMRVVSTYSTAVWMDRIAAINGVNGGPGL TTYLDAALSQQQGTTPEVIEIVIYDLPGRDCAALASNGELPATAAGLQTYETQYIDPIASILSNPK YSSLRIVTIIEPDSLPNAVTNMSIQACATAVPYYEQGIEYALTKLHAIPNVYIYMDAAHSGWLGWP NNASGYVQEVQKVLNASIGVNGIDGFVTNTANYTPLKEPFMTATQQVGGQPVESANFYQWNPDIDE ADYAVDLYSRLVAAGFPSSIGMLIDTLRNGWGGPNEPTGPSTATDVNTFVNQSKIDLRQHRGLWCN QNGAGLGQPPQASPTDFPNAHLDAYVWIKPPGESDGTSAASDPTTGKKSDPMCDPTYTTSYGVLTN ALPNSPIAGQWFPAQFDQLVANARPAV |
| 5 | | CBD_III | VSGGLKVQYKNNDSAPGDNQIKPGLQLVNTGSSSVDLSTVTVRYWFTRDGGSSTLVYNCDWAAMGC GNIRASFGSVNPATPTADTYLQLSFTGGTLAAGGSTGEIQNRVNKSDWSNFTETNDYSYGTNTTFQ DWTKVTVYVNGVLVWGTE |
| 6 | | FN-III | DVTPPSVPTGLVVTGVSGSSVSLAWNASTDNVGVAHYNVYRNGVLVGQPTVTSFTDTGLAAGTAYT YTVAAVDAAGNTSAPSTPV |
| 7 | | CD (GH12) | DCTPGPNQNGVTSVQGDEYRVQTNEWNSSAQQCLTINTATGAWTVSTANFSGGTGGAPATYPSIYK GCHWGNCTTKNVGMPIQISQIGSAVTSWSTTQVSSGAYDVAYDIWTNSTPTTTGQPNGTEIMIWLN SRGGVQPFGSQTATGVTVAGHTWNVWQGQQTSWKIISYVLTPGATSISNLDLKAIFADAAARGSLN TSDYLLDVEAGFEIWQGGQGLGSNSFSVSVTSG |
| 8 | | CBD_II | GVACRATYVVNSDWGSGFTATVTVTNTGSRATNGWTVAWSFGGNQTVTNYWNTALTQSGASVTATN LSYNNVIQPGQSTTFGFNGSYSGTNAAPTLSCTAS |

BRIEF DESCRIPTION OF THE DRAWINGS

FIG. 2 is a graphic representation of the glycoside hydrolase gene/protein families found in various organisms.

DETAILED DESCRIPTION

Definitions

Figure 1:
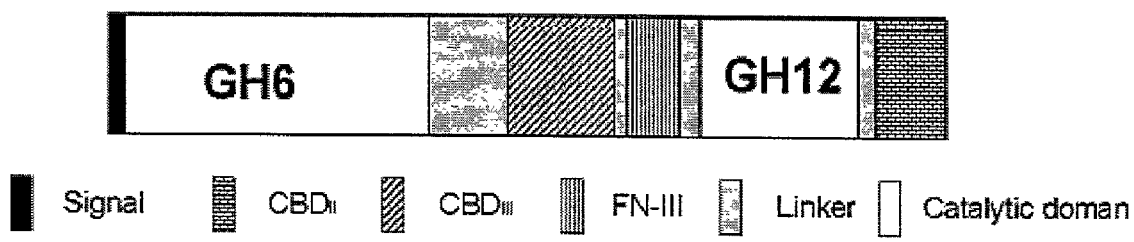
FIG. 1 is a schematic representation of the gene sequence and amino acid segment organization.

The following definitions are provided to facilitate understanding of certain terms used frequently herein and are not meant to limit the scope of the present disclosure:

"Amino acid" refers to any of the twenty naturally occurring amino acids as well as any modified amino acid sequences. Modifications may include natural processes such as posttranslational processing, or may include chemical modifications which are known in the art. Modifications include but are not limited to: phosphorylation, ubiquitination, acetylation, amidation, glycosylatioin, covalent attachment of flavin, ADP-ribosylation, cross linking, iodination, methylation, and alike.

"Antibody" refers to a Y-shaped molecule having a pair of antigen binding sites, a hinge region and a constant region. Fragments of antibodies, for example an antigen binding fragment (Fab), chimeric antibodies, antibodies having a human constant region coupled to a murine antigen binding region, and fragments thereof, as well as other well known recombinant antibodies are included in the present invention.

"Antisense" refers to polynucleotide sequences that are complementary to target "sense" polynucleotide sequence.

"Binding activity" refers to any activity that can be assayed by characterizing the ability of a polypeptide to bind to a substrate. The substrate can be a polymer such as cellulose or can be a complex molecule or aggregate of molecules where the entire moiety comprises at least some cellulose. Note that when used herein the terms cellulose binding domain (CBD) and carbohydrate binding domain are used interchangeably.

"Cellulase activity" refers to any activity that can be assayed by characterizing the enzymatic activity of a cellulase. For example, cellulase activity can be assayed by determining how much reducing sugar is produced during a fixed amount of time for a set amount of enzyme (see Irwin et al., (1998) *J. Bacteriology*, 1709–1714). Other assays are well known in the art and can be substituted.

"Complementary" or "complementarity" refers to the ability of a polynucleotide in a polynucleotide molecule to form a base pair with another polynucleotide in a second polynucleotide molecule. For example, the sequence A-G-T is complementary to the sequence T-C-A. Complementarity may be partial, in which only some of the polynucleotides match according to base pairing, or complete, where all the polynucleotides match according to base pairing.

"Expression" refers to transcription and translation occurring within a host cell. The level of expression of a DNA molecule in a host cell may be determined on the basis of either the amount of corresponding mRNA that is present within the cell or the amount of DNA molecule encoded protein produced by the host cell (Sambrook et al., 1989, *Molecular cloning: A Laboratory Manual*, 18.1–18.88).

"Fusion protein" refers to a first protein having attached a second, heterologous protein. Preferably, the heterologous protein is fused via recombinant DNA techniques, such that the first and second proteins are expressed in frame. The heterologous protein can confer a desired characteristic to the fusion protein, for example, a detection signal, enhanced stability or stabilization of the protein, facilitated oligomerization of the protein, or facilitated purification of the fusion protein. Examples of heterologous proteins useful in the fusion proteins of the invention include molecules having one or more catalytic domains of GuxA, one or more binding domains of GuxA, one or more catalytic domains of a glycoside hydrolase other than GuxA, one or more binding domains of a glycoside hydrolase other than GuxA, or any combination thereof. Further examples include immunoglobulin molecules and portions thereof, peptide tags such as histidine tag (6-His), leucine zipper, substrate targeting moieties, signal peptides, and the like. Fusion proteins are also meant to encompass variants and derivatives of GuxA polypeptides that are generated by conventional site-directed mutagenesis and more modern techniques such as directed evolution, discussed infra.

"Genetically engineered" refers to any recombinant DNA or RNA method used to create a prokaryotic or eukaryotic host cell that expresses a protein at elevated levels, at lowered levels, or in a mutated form. In other words, the host cell has been transfected, transformed, or transduced with a recombinant polynucleotide molecule, and thereby been altered so as to cause the cell to alter expression of the desired protein. Methods and vectors for genetically engineering host cells are well known in the art; for example various techniques are illustrated in Current Protocols in Molecular Biology, Ausubel et al., eds. (Wiley & Sons, New York, 1988, and quarterly updates). Genetically engineering techniques include but are not limited to expression vectors, targeted homologous recombination and gene activation (see, for example, U.S. Pat. No. 5,272,071 to Chappel) and trans activation by engineered transcription factors (see, for example, Segal et al., 1999, *Proc Natl Acad Sci USA* 96(6):2758–63).

"Glycoside hydrolase family" refers to a family of enzymes which hydrolyze the glycosidic bond between two or more carbohydrates or between a carbohydrate and a non-carbohydrate moiety (Henrissat B., (1991) Biochem. J., 280:309–316). Identification of a putative glycoside hydrolase family member is made based on an amino acid sequence comparison and the finding of significant sequence similarity within the putative member's catalytic domain, as compared to the catalytic domains of known family members.

"Homology" refers to a degree of complementarity between polynucleotides, having significant effect on the efficiency and strength of hybridization between polynucleotide molecules. The term also can refer to a degree of similarity between polypeptides.

"Host cell" or "host cells" refers to cells expressing a heterologous polynucleotide molecule. Host cells of the present invention express polynucleotides encoding GuxA or a fragment thereof. Examples of suitable host cells useful in the present invention include, but are not limited to, prokaryotic and eukaryotic cells. Specific examples of such cells include bacteria of the genera *Escherichia, Bacillus,* and *Salmonella*, as well as members of the genera *Pseudomonas, Streptomyces,* and *Staphylococcus*; fungi, particularly filamentous fungi such as *Trichoderma* and *Aspergillus, Phanerochaete chrysosporium* and other white rot fungi; also other fungi including Fusaria, molds, and yeast including Saccharomyces sp., Pichia sp., and Candida sp. and the like; plants e.g. Arabidopsis, cotton, barley, tobacco, potato, and aquatic plants and the like; SF9 insect cells (Summers and Smith, 1987, *Texas Agriculture Experiment Station Bulletin,* 1555), and the like. Other specific examples include mammalian cells such as human embyonic kidney cells (293 cells), Chinese hamster ovary (CHO) cells (Puck et al., 1958, *Proc. Natl. Acad. Sci. USA* 60, 1275–1281), human cervical carcinoma cells (HELA) (ATCC CCL 2), human liver cells (Hep G2) (ATCC HB8065), human breast cancer cells (MCF-7) (ATCC HTB22), human colon carcinoma cells (DLD-1) (ATCC CCL 221), Daudi cells (ATCC CRL-213), murine myeloma cells such as P3/NSI/1-Ag4-1 (ATCC TEB-18), P3X63Ag8 (ATCC TIB-9), SP2/0-Ag14 (ATCC CRL-1581) and the like.

"Hybridization" refers to the pairing of complementary polynucleotides during an annealing period. The strength of hybridization between two polynucleotide molecules is impacted by the homology between the two molecules, stringency of the conditions involved, the melting temperature of the formed hybrid and the G:C ratio within the polynucleotides.

"Identity" refers to a comparison between pairs of nucleic acid or amino acid molecules. Methods for determining sequence identity are known. See, for example, computer programs commonly employed for this purpose, such as the Gap program (Wisconsin Sequence Analysis Package, Version 8 for Unix, Genetics Computer Group, University Research Park, Madison Wis.), that uses the algorithm of Smith and Waterman, 1981, *Adv. Appl. Math.*, 2: 482489.

"Isolated" refers to a polynucleotide or polypeptide that has been separated from at least one contaminant (polynucleotide or polypeptide) with which it is normally associated. For example, an isolated polynucleotide or polypeptide is in a context or in a form that is different from that in which it is found in nature.

"Nucleic acid sequence" refers to the order or sequence of deoxyribonucleotides along a strand of deoxyribonucleic acid. The order of these deoxyribonucleotides determines the order of amino acids along a polypeptide chain. The deoxyribonucleotide sequence thus codes for the amino acid sequence.

"Polynucleotide" refers to a linear sequence of nucleotides. The nucleotides may be ribonucleotides, or deoxyribonucleotides, or a mixture of both. Examples of polynucleotides in the context of the present invention include single and double stranded DNA, single and double stranded RNA, and hybrid molecules having mixtures of single and double stranded DNA and RNA. The polynucleotides of the present invention may contain one or more modified nucleotides.

"Protein," "peptide," and "polypeptide" are used interchangeably to denote an amino acid polymer or a set of two or more interacting or bound amino acid polymers.

"Purify," or "purified" refers to a target protein that is free from at least 5–10% of contaminating proteins. Purification of a protein from contaminating proteins can be accomplished using known techniques, including ammonium sulfate or ethanol precipitation, acid precipitation, heat precipitation, anion or cation exchange chromatography, phosphocellulose chromatography, hydrophobic interaction chromatography, affinity chromatography, hydroxylapatite chromatography, size-exclusion chromatography, and lectin chromatography. Various protein purification techniques are illustrated in *Current Protocols in Molecular Biology*, Ausubel et al., eds. (Wiley & Sons, New York, 1988, and quarterly updates).

"Selectable marker" refers to a marker that identifies a cell as having undergone a recombinant DNA or RNA event. Selectable markers include, for example, genes that encode antimetabolite resistance such as the DHFR protein that confers resistance to methotrexate (Wigler et al, 1980, *Proc Natl Acad Sci USA* 77:3567; O'Hare et al., 1981, *Proc Natl Acad Sci USA,* 78:1527), the GPT protein that confers resistance to mycophenolic acid (Mulligan & Berg, 1981, PNAS USA, 78:2072), the neomycin resistance marker that confers resistance to the aminoglycoside G-418 (Calberre-Garapin et al., 1981, *J Mol Biol,* 150:1), the Hygro protein that confers resistance to hygromycin (Santerre et al., 1984, *Gene* 30:147), and the Zeocin™ resistance marker (Invitrogen). In addition, the herpes simplex virus thymidine kinase, hypoxanthine-guanine phosphoribosyltransferase and adenine phosphoribosyltransferase genes can be employed in tk⁻, hgprt⁻ and aprt⁻ cells, respectively.

"Stringency" refers to the conditions (temperature, ionic strength, solvents, etc) under which hybridization between polynucleotides occurs. A hybridzation reaction conducted under high stringency conditions is one that will only occur between polynucleotide molecules that have a high degree of complementary base pairing (85% to 100% identity). Conditions for high stringency hybridization, for example, may include an overnight incubation at about 42° C. for about 2.5 hours in 6×SSC/0.1% SDS, followed by washing of the filters in 1.0×SSC at 65° C., 0.1% SDS. A hybridization reaction conducted under moderate stringency conditions is one that will occur between polynucleotide molecules that have an intermediate degree of complementary base pairing (50% to 84% identity).

"Substrate targeting moiety" refers to any signal on a substrate, either naturally occurring or genetically engineered, used to target any GuxA polypeptide or fragment thereof to a substrate. Such targeting moieties include ligands that bind to a substrate structure. Examples of ligand/receptor pairs include cellulose binding domains and cellulose. Many such substrate-specific ligands are known and are useful in the present invention to target a GuxA polypeptide or fragment thereof to a substrate. A novel example is a GuxA cellulose binding domain that is used to tether other molecules to a cellulose-containing substrate such as a fabric. "Thermal tolerant" refers to the property of withstanding partial or complete inactivation by heat and can also be described as thermal resistance or thermal stability. Although some variation exists in the literature, the following definitions can be considered typical for the optimum temperature range of stability and activity for enzymes: psychrophilic (below freezing to 10C); mesophilic (10° C. to 50° C.); thermophilic (50° C. to 75° C.); and caldophilic (75° C. to above boiling water temperature). The stability and catalytic activity of enzymes are linked characteristics, and the ways of measuring these properties vary considerably. For industrial enzymes, stability and activity are best measured under use conditions, often in the presence of substrate. Therefore, cellulases that must act on process streams of cellulose must be able to withstand exposure up to thermophilic or even caldophilic temperatures for digestion times in excess of several hours.

In encompassing a wide variety of potential applications for embodiments of the present invention, thermal tolerance refers to the ability to function in a temperature range of from about 15° C. to about 100° C. A preferred range is from about 30° C. to about 80° C. A highly preferred range is from about 50° C. to about 70° C. For example, a protein that can function at about 45° C. is considered in the preferred range even though it may be susceptible to partial or complete inactivation at temperatures in a range above about 45° C. and less than about 80° C. For polypeptides derived from organisms such as Acidothermus, the desirable property of thermal tolerance among is often accompanied by other desirable characteristics such as: resistance to extreme pH degradation, resistance to solvent degradation, resistance to proteolytic degradation, resistance to detergent degradation, resistance to oxidizing agent degradation, resistance to chaotropic agent degradation, and resistance to general degradation. Cowan D A in Danson M J et al. (1992) *The Archaebacterial, Biochemistry and Biotechnology* at 149–159, University Press, Cambridge, ISBN 1855780100. Here 'resistance' is intended to include any partial or complete level of residual activity. When a polypeptide is described as thermal tolerant it is understood that any one, more than one, or none of these other desirable properties can be present.

"Variant", as used herein, means a polynucleotide or polypeptide molecule that differs from a reference molecule. Variants can include nucleotide changes that result in amino acid substitutions, deletions, fusions, or truncations in the resulting variant polypeptide when compared to the reference polypeptide.

"Vector," "extra-chromosomal vector" or "expression vector" refers to a first polynucleotide molecule, usually double-stranded, which may have inserted into it a second polynucleotide molecule, for example a foreign or heterologous polynucleotide. The heterologous polynucleotide molecule may or may not be naturally found in the host cell, and may be, for example, one or more additional copy of the heterologous polynucleotide naturally present in the host genome. The vector is adapted for transporting the foreign polynucleotide molecule into a suitable host cell. Once in the host cell, the vector may be capable of integrating into the host cell chromosomes. The vector may optionally contain additional elements for selecting cells containing the integrated polynucleotide molecule as well as elements to promote transcription of mRNA from transfected DNA. Examples of vectors useful in the methods of the present invention include, but are not limited to, plasmids, bacteriophages, cosmids, retroviruses, and artificial chromosomes.

Within the application, unless otherwise stated, the techniques utilized may be found in any of several well-known references, such as: *Molecular Cloning: A Laboratory Manual* (Sambrook et al. (1989) Molecular cloning: A Laboratory Manual), *Gene Expression Technology* (Methods in Enzymology, Vol. 185, edited by D. Goeddel, 1991 Academic Press, San Diego, Calif.), "Guide to Protein Purification" in *Methods in Enzymology* (M. P. Deutshcer, 3d., (1990) Academic Press, Inc.), *PCR Protocols: A Guide to Methods and Applications* (Innis et al. (1990) Academic Press, San Diego, Calif.), Culture of Animal Cells: A Manual of Basic Technique, $2^{nd}$ ed. (R. I. Freshney (1987) Liss, Inc., New York, N.Y.), and *Gene Transfer and Expression Protocols*, pp 109–128, ed. E. J. Murray, The Humana Press Inc., Clifton, N.J.).

O-Glycoside Hydrolases

Glycoside hydrolases are a large and diverse family of enzymes that hydrolyse the glycosidic bond between two carbohydrate moieties or between a carbohydrate and a non-carbohydrate moiety (See FIG. 2). Glycoside hydrolase enzymes are classified into glycoside hydrolase (GH) families based on significant amino acid similarities within their catalytic domains. Enzymes having related catalytic domains are grouped together within a family, (Henrissat et al., (1991) supra, and Henrissat et al. (1996), Biochem. J. 316:695–696), where the underlying classification provides a direct relationship between the GH domain amino acid sequence and how a GH domain will fold. This information ultimately provides a common mechanism for how the enzyme will hydrolyse the glycosidic bond within a substrate, i.e., either by a retaining mechanism or inverting mechanism (Henrissat., B, (1991) supra).

Cellulases belong to the GH family of enzymes. Cellulases are produced by a variety of bacteria and fungi to degrade the beta-(1,4)-glycosidic bond of cellulose and to so produce successively smaller fragments of cellulose and ultimately produce glucose. At present, cellulases are found within are at least 11 different GH families. Three different types of cellulase enzyme activities have been identified within these GH families: exo-acting cellulases which cleave successive disaccharide units from the non-reducing ends of a cellulose chain; endo-acting cellulases which randomly cleave successive disaccharide units within the cellulose chain; and β-glucosidases which cleave successive disaccharide units to glucose (J. W. Deacon, (1997) Modern Mycology, 3rd Ed., ISBN: 0-632-03077-1. 97–98).

Many cellulases are characterized by having a multiple domain unit within their overall structure, a GH or catalytic domain is joined to a cellulose-binding domain (CBD) by a glycosylated linker peptide (see FIG. 1) (Koivula et al., (1996) Protein Expression and Purification 8:391–400). As noted above, cellulases do not belong to any one family of GH domains, but rather have been identified within at least 11 different GH families to date. The CBD type domain increases the concentration of the enzyme on the substrate, in this case cellulose, and the linker peptide provides flexibility for both larger domains.

Conversion of cellulose to glucose is an essential step in the production of ethanol or other biofuels from biomass. Cellulases are an important component of this process, where approximately one kilogram of cellulase can digest fifty kilograms of cellulose. Within this process, thermostable cellulases have taken precedent, due to their ability to function at elevated temperatures and under other conditions including pH extremes, solvent presence, detergent presence, proteolysis, etc. (see Cowan D A (1992), supra).

Highly thermostable cellulase enzymes are secreted by the cellulolytic themophile *Acidothermus cellulolyticus* (U.S. Pat. Nos. 5,275,944 and 5,110,735). This bacterium was originally isolated from decaying wood in an acidic, thermal pool at Yellowstone National Park and deposited with the American Type Culture Collection (ATCC 43068) (Mohagheghi et al., (1986) *Int. J. System. Bacteriol.*, 36:435–443).

Recently, a thermostable cellulase, E1 endoglucanase, was identified and characterized from *Acidothermus cellulolyticus* (U.S. Pat. No. 5,536,655). The E1 endoglucanase has maximal activity between 75 and 83° C. and is active to a pH well below 5. Thermostable cellulase, and E1 endoglucanase, are useful in the conversion of biomass to biofuels, and in particular, are useful in the conversion of cellulose to glucose. Conversion of biomass to biofuel represents an extremely important alternative fuel source that is more environmentally friendly than conventional fuels, and provides a use, in some cases, for waste products.

GuxA

As described more fully in the Examples below, GuxA, a novel thermostable cellulase, has now been identified and characterized. The predicted amino acid sequence of GuxA (SEQ ID NO: 1) has an organization characteristic of a cellulase enzyme. GuxA contains two catalytic domain-linker domain-cellulose binding domain units, separated from each other by a centrally located fibronectin domain. In particular, a first unit is located at the N-terminal end of the protein and includes a GH6 domain (amino acids 54–476)-linker-$CBD_{III}$ (amino acids 584–733), and a second unit, that includes a GH12 domain, is located at the C-terminal end of the protein (amino acids 860–1090)4inker-$CBD_{II}$ (amino acids 1128–1228). As discussed in more detail below, significant amino acid similarity of GuxA to other cellulases identifies GuxA as a cellulase.

GuxA, as noted above, has two catalytic domains, identified as belonging to the GH6 and GH12 families. The GH6 domain family includes a number of cellobiohydrolases, for example, exocellobiohydrolase A isolated from *Cellulomonas fimi*, and exoglucanase E3 isolated from *Thermobifida fusca*. The GH6 members degrade substrate using an inverting mechanism. The GH12 domain family includes a number of endoglucanases, for example, endo-1,4-glucanase isolated from *Streptomyces lividans*, and endo-1,4-glucanase S cellulase 12A isolated from Streptomyces sp. 11AG8. The GH12 members degrade substrate using a retaining mechanism.

Being a member of the GH6 and GH12 family of proteins identifies GuxA as potentially having both exoglucanase and endoglucanase activity. In addition, the predicted amino acid sequence (SEQ ID NO: 2) indicates that CBD type II and CBD type III domains are present as characterized by Tomme P. et al. (1995), in Enzymatic Degradation of Insoluble Polysaccharides (Saddler J N & Penner M, eds.), at 142–163, American Chemical Society, Washington. See also Tomme, P. & Claeyssens, M. (1989) FEBS Lett. 243, 239–2431; Gilkes, N. R et al., (1988) J.Biol.Chem. 263, 10401–10407.

GuxA is also a thermostable cellulase as it is produced by the themophile *Acidothermus cellulolyticus*. As discussed, GuxA polypeptides can have other desirable characteristics (see Cowan D A (1992), supra). Like other members of the cellulase family, and in particular thermostable cellulases, GuxA polypeptides are useful in the conversion of biomass to biofuels and biofuel additives, and in particular, biofuels from cellulose. It is envisioned that GuxA polypeptides could be used for other purposes, for example in detergents, pulp and paper processing, food and feed processing, and in textile processes. GuxA polypeptides can be used alone or in combination with one or more other cellulases or glycoside hydrolases to perform the uses described herein or known within the relevant art, all of which are within the scope of the present disclosure.

GuxA Polypeptides

GuxA polypeptides of the invention include isolated polypeptides having an amino acid sequence as shown below in Example 1; Table 1 and in SEQ ID NO:1, as well as variants and derivatives, including fragments, having substantial identity to the amino acid sequence of SEQ ID NO:1 and that retain any of the functional activities of GuxA. GuxA polypeptide activity can be determined, for example, by subjecting the variant, derivative, or fragment to a substrate binding assay or a cellulase activity assay such as those described in Irwin D et al., J. Bacteriology 180(7): 1709–1714 (April 1998).

TABLE 1

GuxA amino acid sequence.

(SEQ ID NO: 1)
MERTQQSGRNCRYQRGTTRMPAISKRLRAGVLAGAVSIAASIVPLAMQHP

AIAATHVDNPYAGATFFVNPYWAQEVQSEAANQTNATLAAKMRVVSTYST

AVWMDRIAAINGVNGGPGLTTYLDAALSQQQGTTPEVIEIVIYDLPGRDC

AALASNGELPATAAGLQTYETQYIDPIASILSNPKYSSLRIVTIIEPDSL

PNAVTNMSIQACATAVPYYEQGIEYALTKLHAIPNVYIYMDAAHSGWLGW

PNNASGYVQEVQKVLNASIGVNGIDGFVTNTANYTPLKEPFMTATQQVGG

TABLE 1-continued

GuxA amino acid sequence.

QPVESANFYQWNPDIDEADYAVDLYSRLVAAGFPSSIGMLIDTLRNGWGG

PNEPTGPSTATDVNTFVNQSKIDLRQHRGLWCNQNGAGLGQPPQASPTDF

PNAHLDAYVWIKPPGESDGTSAASDPTTGKKSDPMCDPTYTTSYGVLTNA

LPNSPIAGQWFPAQFDQLVANARPAVPTSTSSSPPPPPPSPSASPSPSPS

PSPSSSPSPSPSPSSSPSPSPSPSPSPSSSPSPSPSSSPSPSPSPSPSPS

SSPSPSPSSSPSPSPSPSPSSSPSPSPTSSPVSGGLKVQYKNNDSAPG

DNQIKPGLQLVNTGSSSVDLSTVTVRYWFTRDGGSSTLVYNCDWAAMGCG

NIRASFGSVNPATPTADTYLQLSFTGGTLAAGGSTGEIQNRVNKSDWSNF

TETNDYSYGTNTTFQDWTKVTVYVNGVLVWGTEPSGTSPSPTPSPSPSPS

PSPGGDVTPPSVPTGLVVTGVSGSSVSLAWNASTDNVGVAHYNVYRNGVL

VGQPTVTSFTDTGLAAGTAYTYTVAAVDAAGNTSAPSTPVTATTTSPSPS

PTPTGTTVTDCTPGPNQNGVTSVQGDEYRVQTNEWNSSAQQCLTINTATG

AWTVSTANFSGGTGGAPATYPSIYKGCHWGNCTTKNVGMPIQISQIGSAV

TSWSTTQVSSGAYDVAYDIWTNSTPTTTGQPNGTEIMIWLNSRGGVQPFG

SQTATGVTVAGHTWNVWQGQQTSWKIISYVLTPGATSISNLDLKAIFADA

AARGSLNTSDYLLDVEAGFEIWQGGQGLGSNSFSVSVTSGTSSPTPSPSP

TPTPSPTPTPSPSPTPSPSPTSSPSSSGVACRATYVVNSDWGSGFTATVT

VTNTGSRATNGWTVAWSFGGNQTVTNYWNTALTQSGASVTATNLSYNNVI

QPGQSTTFGFNGSYSGTNAAPTLSCTAS

As listed and described in Tables 1 and 5, the isolated GuxA polypeptide includes an N-terminal hydrophobic region that functions as a signal peptide, having an amino acid sequence that begins with Met1 and extends to about Ala53; a first catalytic domain having significant sequence similarity to a GH6 family domain that begins with about Ala54 and extends to about Val476, a cellulose binding domain type III region that begins with about Val584 and extends to about Glu733, a fibronectin type m domain that begins with about Asp756 and extends to about Val840, a second catalytic domain having significant sequence similarity to a GH12 family domain that begins with about Asp860 and extends to about Gly1090, and a cellulose binding domain type II that begins with about Gly1128 and extends to about Ser1228. Variants and derivatives of GuxA include, for example, GuxA polypeptides modified by covalent or aggregative conjugation with other chemical moieties, such as glycosyl groups, polyethylene glycol (PEG) groups, lipids, phosphate, acetyl groups, and the like.

The amino acid sequence of GuxA polypeptides of the invention is in some embodiements about 60% identical, and in other embodiements about 70% identical, or in some embodiments about 90% identical, to the GuxA amino acid sequence shown above in Table 1 and SEQ ID NO: 1. The percentage identity, also termed homology (see definition above) can be readily determined, for example, by comparing the two polypeptide sequences using any of the computer programs commonly employed for this purpose, such as the Gap program (Wisconsin Sequence Analysis Package, Version 8 for Unix, Genetics Computer Group, University Research Park, Madison Wis.), which uses the algorithm of Smith and Waterman, 1981, Adv. AppL Math. 2: 482489.

Variants and derivatives of the GuxA polypeptide may further include, for example, fusion proteins formed of a GuxA polypeptide and a heterologous polypeptide. Preferred heterologous polypeptides include those that facilitate purification, oligomerization, stability, or secretion of the GuxA polypeptides.

GuxA polypeptide fragments may include, but are not limited to, the polypeptide sequences listed in Table 5, SEQ ID NOS: 3, 4, 5, 6, 7 and 8.

GuxA polypeptide variants and derivatives, as used in the description of the invention, can contain conservatively substituted amino acids, meaning that one or more amino acid can be replaced by an amino acid that does not alter the secondary and/or tertiary structure of the polypeptide. Such substitutions can include the replacement of an amino acid, by a residue having similar physicochemical properties, such as substituting one aliphatic residue (Ile, Val, Leu, or Ala) for another, or substitutions between basic residues Lys and Arg, acidic residues Glu and Asp, amide residues Gln and Asn, hydroxyl residues Ser and Tyr, or aromatic residues Phe and Tyr. Phenotypically silent amino acid exchanges are described more fully in Bowie et al., 1990, Science 247: 1306–1310. In addition, functional GuxA polypeptide variants include those having amino acid substitutions, deletions, or additions to the amino acid sequence outside functional regions of the protein, for example, outside the catalytic and cellulose binding domains. These would include, for example, the various linker sequences that connect functional domains as defined herein.

The GuxA polypeptides of the present invention are preferably provided in an isolated form, and preferably are substantially purified. The polypeptides may be recovered and purified from recombinant cell cultures by known methods, including, for example, ammonium sulfate or ethanol precipitation, anion or cation exchange chromatography, phosphocellulose chromatography, hydrophobic interaction chromatography, affinity chromatography, hydroxylapatite chromatography, and lectin chromatography. Preferably, high performance liquid chromatography (HPLC) is employed for purification.

Another embedment of the invention provides for a form of GuxA polypeptide and polypeptides that are recombinant polypeptides expressed by suitable hosts. Furthermore, the hosts can simultaneously produce other cellulases such that a mixture is produced comprising a GuxA polypeptide and one or more other cellulases. Such a mixture can be effective in crude fermentation processing or other industrial processing.

GuxA polypeptides can be fused to heterologous polypeptides to facilitate purification. Many available heterologous peptides (peptide tags) allow selective binding of the fusion protein to a binding partner. Non-limiting examples of peptide tags include 6-His, thioredoxin, hemaglutinin, GST, and the OmpA signal sequence tag. A binding partner that recognizes and binds to the heterologous peptide can be any molecule or compound, including metal ions (for example, metal affinity columns), antibodies, antibody fragments, or any protein or peptide that preferentially binds the heterologous peptide to permit purification of the fusion protein.

GuxA polypeptides can be modified to facilitate formation of GuxA oligomers. For example, GuxA polypeptides can be fused to peptide moieties that promote oligomerization, such as leucine zippers and certain antibody fragment polypeptides, for example, Fc polypeptides. Techniques for preparing these fusion proteins are known, and are described, for example, in WO 99/31241 and in Cosman et.al., 2001 *Immunity* 14:123–133. Fusion to an Fc polypeptide offers the additional advantage of facilitating purification by affinity chromatography over Protein A or Protein G columns. Fusion to a leucine-zipper (LZ), for example, a repetitive heptad repeat, often with four or five leucine residues interspersed with other amino acids, is described in Landschultz et al., 1988, *Science,* 240:1759.

It is also envisioned that an expanded set of variants and derivatives of GuxA polynucleotides and/or polypeptides can be generated to select for useful molecules, where such expansion is achieved not only by conventional methods such as site-directed mutagenesis (SDM) but also by more modem techniques, either independently or in combination.

Site-directed-mutagenesis is considered an informational approach to protein engineering and can rely on high-resolution crystallographic structures of target proteins and some stratagem for specific amino acid changes (Van Den Burg, B.; Vriend, G.; Veltman, O. R.; Venema, G.; Eijsink, V. G. H. Proc. Nat. Acad. Sci. U.S. 1998, 95, 2056–2060). For example, modification of the amino acid sequence of GuxA polypeptides can be accomplished as is known in the art, such as by introducing mutations at particular locations by oligonucleotide-directed mutagenesis (Walder et al., 1986, Gene, 42:133; Bauer et al., 1985, Gene 37:73; Craik, 1985, BioTechniques, 12–19; Smith et al., 1981, Genetic Engineering: Principles and Methods, Plenum Press; and U.S. Pat. No. 4,518,584 and U.S. Pat. No. 4,737,462). SDM technology can also employ the recent advent of computational methods for identifying site-specific changes for a variety of protein engineering objectives (Hellinga, H. W. Nature Structural. Biol. 1998, 5, 525–527).

The more modern techniques include, but are not limited to, non-informational mutagenesis techniques (referred to generically as "directed evolution"). Directed evolution, in conjunction with high-throughput screening, allows testing of statistically meaningful variations in protein conformation (Arnold, F. H. Nature Biotechnol. 1998, 16, 617–618). Directed evolution technology can include diversification methods similar to that described by Crameri A. et al. (1998, Nature 391: 288–291), site-saturation mutagenesis, staggered extension process (STEP) (Zhao, H.; Giver, L.; Shao, Z.; Affholter, J. A.; Arnold, F. H. Nature Biotechnol. 1998, 16, 258–262), and DNA synthesis/reassembly (U.S. Pat. No. 5,965,408).

Fragments of the GuxA polypeptide can be used, for example, to generate specific anti-GuxA antibodies. Using known selection techniques, specific epitopes can be selected and used to generate monoclonal or polyclonal antibodies. Such antibodies have utlilty in the assay of GuxA activity as well as in purifying recombinant GuxA polypeptides from genetically engineered host cells.

GuxA Polynucleotides

The invention also provides polynucleotide molecules encoding the GuxA polypeptides discussed above. GuxA polynucleotide molecules of the invention include polynucleotide molecules having the nucleic acid sequence shown in Table 2 and SEQ ID NO: 2, polynucleotide molecules that hybridize to the nucleic acid sequence of Table 2 and SEQ ID NO: 2 under high stringency hybridization conditions (for example, 42°, 2.5 hr., 6×SCC, 0.1%SDS); and polynucleotide molecules having substantial nucleic acid sequence identity with the nucleic acid sequence of Table 2 and SEQ ID NO: 2, particularly with those nucleic acids encoding the two catalytic domains, GH6 (from amino acid 54 to 476) and GH12 (from amino acid 860 to 1090), the cellulose binding domain III (from amino acid 584 to 733) and cellulose binding domain II (from amino acid 1128 to 1228).

TABLE 2

GuxA nucleotide sequence.

(SEQ ID NO: 2)
ATGGAGCGAACCCAACAATCCGGACGGAACTGCAGGTACCAGAGAGGAAC

GACACGAATGCCCGCCATCTCAAAACGGCTGCGAGCCGGCGTCCTCGCCG

GGGCGGTGAGCATCGCAGCCTCCATCGTGCCGCTGGCGATGCAGCATCCT

GCCATCGCCGCGACGCACGTCGACAATCCCTATGCGGGAGCGACCTTCTT

CGTCAACCCGTACTGGGCGCAAGAAGTACAGAGCGAAGCGGCGAACCAGA

CCAATGCCACTCTCGCAGCGAAAATGCGCGTCGTTTCCACATATTCGACG

GCCGTCTGGATGGACCGCATCGCTGCGATCAACGGCGTCAACGGCGGACC

CGGCTTGACGACATATCTGGACGCCGCCCTCTCCCAGCAGCAGGGAACCA

CCCCTGAAGTCATTGAGATTGTCATCTACGATCTGCCGGGACGCGACTGC

GCGGCGCTCGCCTCCAACGGCGAACTGCCCGCTACGGCAGCAGGTTTGCA

GACCTATGAAACGCAGTACATCGATCCGATTGCGAGTATCCTGAGCAATC

CGAAGTACTCCAGCCTGCGGATCGTGACGATCATTGAGCCGGACTCGCTG

CCAAACGCGGTCACCAATATGAGCATTCAAGCGTGTGCAACGGCGGTGCC

GTATTACGAGCAAGGCATCGAGTACGCGCTCACGAAATTGCACGCCATTC

CGAACGTGTACATCTACATGGACGCCGCCCACTCCGGCTGGCTTGGGTGG

CCCAATAATGCCAGCGGATACGTACAGGAAGTCCAGAAGGTCCTCAACGC

GAGCATCGGGGTCAACGGCATCGACGGCTTCGTCACCAACACGGCGAATT

ACACGCCGTTGAAGGAGCCGTTCATGACCGCCACCCAGCAGGTCGGCGGA

CAGCCGGTGGAGTCGGCGAATTTCTACCAGTGGAATCCTGACATCGACGA

AGCCGACTACGCGGTTGACTTGTACTCGCGGCTCGTCGCCGCTGGCTTTC

CAAGCAGCATCGGCATGCTCATCGACACCTTACGCAACGGTTGGGGTGGT

CCGAACGAACCAACAGGCCCGAGCACCGCGACCGATGTCAACACCTTCGT

CAACCAGTCGAAGATTGACCTTCGGCAGCACCGCGGCCTGTGGTGCAACC

AGAACGGTGCGGGCCTCGGCCAGCCGCCGCAGGCAAGCCCGACGGACTTC

CCGAACGCGCACCTCGACGCGTATGTCTGGATCAAGCCGCCGGGTGAGTC

GGACGGCACAAGCGCTGCGAGCGATCCGACAACTGGCAAGAAGTCGGACC

CCATGTGCGACCCGACGTACACGACGTCGTACGGGGTACTGACCAACGCG

TTACCGAACTCCCCGATCGCCGGCCAGTGGTTCCCGGCGCAGTTTGACCA

GCTTGTCGCGAACGCACGGCCAGCGGTGCCGACGTCGACCAGCTCGAGCC

CGCCGCCTCCGCCGCCGAGTCCGTCGGCTTCGCCGAGTCCGAGCCCGAGT

CCGAGCCCGAGCAGCTCGCCATCGCCGTCGCCGTCTCCGAGCTCGAGCCC

GTCTCCGTCGCCGAGCCCGAGTCCGAGCCCGAGTAGCTCGCCGTCGCCGT

CTCCGAGCTCGAGCCCGTCTCCGTCGCCGAGCCCGAGTCCGAGCCCGAGT

AGCTCGCCGTCGCCGTCTCCGAGCTCGAGCCCGTCTCCGTCGCCGAGCCC

GAGTCCGAGCCCGAGTAGCTCGCCGTCGCCGTCTCCGACGTCGTCGCCGG

TGTCGGGTGGGCTGAAGGTGCAGTACAAGAACAATGATTCGGCGCCGGGT

TABLE 2-continued

GuxA nucleotide sequence.

GATAACCAGATCAAACCGGGTCTCCAGTTGGTGAATACCGGGTCGTCGTC
GGTGGATTTGTCGACGGTGACGGTGCGGTACTGGTTCACCCGGGATGGTG
GGTCGTCGACACTGGTGTACAACTGTGACTGGGCGGCGATGGGGTGTGGG
AATATCCGCGCCTCGTTCGGCTCGGTGAACCCGGCGACGCCGACGGCGGA
CACCTACCTGCAGTTGTCGTTCACTGGTGGAACGTTGGCCGCTGGTGGGT
CGACGGGTGAGATTCAAAACCGGGTGAATAAGAGTGACTGGTCGAATTTC
ACCGAGACCAATGACTACTCGTATGGGACGAACACCACCTTCCAGGACTG
GACGAAGGTGACGGTGTACGTCAACGGCGTGTTGGTGTGGGGACTGAAC
CGTCCGGCACCAGCCCCAGCCCCACACCATCCCCGAGCCCGAGCCCGAGC
CCGAGCCCGGGTGGGGATGTGACGCCGCCGAGTGTGCCGACCGGCTTGGT
GGTGACGGGGGTGAGTGGGTCGTCGGTGTCGTTGGCGTGGAATGCGTCGA
CGGATAACGTGGGGGTGGCGCATTACAACGTGTACCGCAACGGGGTGTTG
GTGGGCCAGCCGACGGTGACCTCGTTCACCGACACGGGTTTGGCCGCGGG
AACCGCGTACACCTACACGGTGGCCGCGGTGGACGCTGCGGGTAACACCT
CCGCCCCATCCACCCCCGTCACCGCCACCACCACGAGTCCCAGCCCCAGC
CCCACGCCGACGGGGACCACGGTCACCGACTGCACGCCCGGTCCTAACCA
GAATGGTGTGACCAGCGTGCAGGGCGACGAATACCGGGTGCAGACCAATG
AGTGGAATTCGTCGGCCCAGCAGTGCCTCACCATCAATACCGCGACCGGT
GCCTGGACGGTGAGCACTGCGAACTTCAGCGGTGGGACCGGCGGTGCGCC
CGCGACGTATCCGTCGATCTACAAGGGCTGCCACTGGGGCAACTGCACCA
CGAAGAACGTCGGGATGCCGATTCAGATCAGTCAGATTGGTTCGGCTGTG
ACGTCGTGGAGTACGACGCAGGTGTCGTCGGGCGCGTATGACGTGGCCTA
CGACATTTGGACGAACAGTACCCCAACGACAACCGGTCAGCCAAACGGTA
CCGAAATCATGATTTGGCTGAATTCGCGTGGTGGGGTGCAGCCGTTCGGG
TCGCAGACAGCGACGGGTGTGACGGTCGCTGGTCACACGTGGAATGTCTG
GCAGGGTCAGCAGACCTCGTGGAAGATTATTTCCTACGTCCTGACCCCCG
GTGCGACGTCGATCAGTAATCTGGATTTGAAGGCGATTTTCGCGGACGCC
GCGGCACGCGGGTCGCTCAACACCTCCGATTACCTGCTCGACGTTGAGGC
CGGGTTTGAGATCTGGCAAGGTGGTCAGGGCCTGGGCAGCAACTCGTTCA
GCGTCTCCGTGACGAGCGGCACGTCCAGCCCGACACCGAGCCCGAGCCCG
ACGCCGACACCGAGCCCGACGCCGACACCGTCTCCGAGCCCGACCCCGTC
GCCGAGTCCGACCAGCTCGCCGTCGTCGTCGGGTGTGGCGTGCCGGGCGA
CGTATGTGGTGAATAGTGATTGGGGTTCTGGGTTTACGGCGACGGTGACG
GTGACGAATACCGGGAGCCGGGCGACGAACGGGTGGACGGTGGCGTGGTC
GTTTGGTGGGAATCAGACGGTCACGAACTACTGGAACACTGCGTTGACCC
AATCAGGTGCATCGGTGACGGCGACGAACCTGAGTTACAACAACGTGATC
CAACCGGGTCAGTCGACCACCTTCGGATTCAACGGAAGTTACTCAGGAAC
AAACGCCGCGCCGACGCTCAGCTGCACAGCCAGCTGA

The GuxA polynucleotide molecules of the invention are preferably isolated molecules encoding the GuxA polypetide having an amino acid sequence as shown in Table 1 and SEQ ID NO: 1, as well as derivatives, variants, and useful fragments of the GuxA polynucleotide. The GuxA polynucleotide sequence can include deletions, substitutions, or additions to the nucleic acid sequence of Table 2 and SEQ ID NO: 2.

The GuxA polynucleotide molecule of the invention can be cDNA, chemically synthesized DNA, DNA amplified by PCR, RNA, or combinations thereof. Due to the degeneracy of the genetic code, two DNA sequences may differ and yet encode identical amino acid sequences. The present invention thus provides an isolated polynucleotide molecule having a GuxA nucleic acid sequence encoding GuxA polypeptide, where the nucleic acid sequenc encodes a polypeptide having the complete amino acid sequences as shown in Table 1 and SEQ ID NO: 1, or variants, derivatives, and fragments thereof.

The GuxA polynucleotides of the invention have a nucleic acid sequence that is in some embodiments about 60% identical to the nucleic acid sequence shown in Table 2 and SEQ ID NO: 2, in some embodiments about 70% identical to the nucleic acid sequence shown in Table 2 and SEQ ID NO: 2, and in other embodiments about 90% identical to the nucleic acid sequence shown in Table 2 and SEQ ID NO: 2. Nucleic acid sequence identity is determined by known methods, for example by aligning two sequences in a software program such as the BLAST program (Altschul, S. F et al. (1990) J. Mol. Biol. 215:403–410, from the National Center for Biotechnology Information (http://www.ncbi.nlm.nih.gov/BLAST/).

The GuxA polynucleotide molecules of the invention also include isolated polynucleotide molecules having a nucleic acid sequence that hybridizes under high stringency conditions (as defined above) to a the nucleic acid sequence shown in Table 2 and SEQ ID NO: 2. Hybridization of the polynucleotide is to at least about 15 contiguous nucleotides, or at least about 20 contiguous nucleotides, and in other embodiments at least about 30 contiguous nucleotides, and in still other embodiments at least about 100 contiguous nucleotides of the nucleic acid sequence shown in Table 2 and SEQ ID NO: 2.

Useful fragments of the GuxA-encoding polynucleotide molecules described herein, include probes and primers. Such probes and primers can be used, for example, in PCR methods to amplify and detect the presence of GuxA polynucleotides in vitro, as well as in Southern and Northern blots for analysis of GuxA. Cells expressing the GuxA polynucleotide molecules of the invention can also be identified by the use of such probes. Methods for the production and use of such primers and probes are known. For PCR, 5' and 3' primers corresponding to a region at the termini of the GuxA polynucleotide molecule can be employed to isolate and amplify the GuxA polynucleotide using conventional techniques.

Other useful fragments of the GuxA polynucleotides include antisense or sense oligonucleotides comprising a single-stranded nucleic acid sequence capable of binding to a target GuxA mRNA (using a sense strand), or DNA (using an antisense strand) sequence.

Vectors and Host Cells

The present invention also provides vectors containing the polynucleotide molecules of the invention, as well as host cells transformed with such vectors. Any of the polynucleotide molecules of the invention may be contained in a vector, which generally includes a selectable marker and an origin of replication, for propagation in a host. The vectors further include suitable transcriptional or translational regulatory sequences, such as those derived from a mammalian, microbial, viral, or insect genes, operably linked to the GuxA polynucleotide molecule. Examples of such regulatory sequences include transcriptional promoters, operators, or enhancers, MRNA ribosomal binding sites, and appropriate sequences which control transcription and translation. Nucleotide sequences are operably linked when the regulatory sequence functionally relates to the DNA encoding the target protein. Thus, a promoter nucleotide sequence is operably linked to a GuxA DNA sequence if the promoter nucleotide sequence directs the transcription of the GuxA sequence.

Selection of suitable vectors for the cloning of GuxA polynucleotide molecules encoding the target GuxA polypeptides of this invention will depend upon the host cell in which the vector will be transformed, and, where applicable, the host cell from which the target polypeptide is to be expressed. Suitable host cells for expression of GuxA polypeptides include prokaryotes, yeast, and higher eukaryotic cells, each of which is discussed below.

The GuxA polypeptides to be expressed in such host cells may also be fusion proteins that include regions from heterologous proteins. As discussed above, such regions may be included to allow, for example, secretion, improved stability, or facilitated purification of the GuxA polypeptide. For example, a nucleic acid sequence encoding an appropriate signal peptide can be incorporated into an expression vector. A nucleic acid sequence encoding a signal peptide (secretory leader) may be fused in-frame to the GuxA sequence so that GuxA is translated as a fusion protein comprising the signal peptide. A signal peptide that is functional in the intended host cell promotes extracellular secretion of the GuxA polypeptide. Preferably, the signal sequence will be cleaved from the GuxA polypeptide upon secretion of GuxA from the cell. Non-limiting examples of signal sequences that can be used in practicing the invention include the yeast I-factor and the honeybee melatin leader in Sf9 insect cells.

Suitable host cells for expression of target polypeptides of the invention include prokaryotes, yeast, and higher eukaryotic cells. Suitable prokaryotic hosts to be used for the expression of these polypeptides include bacteria of the genera Escherichia, Bacillus, and Salmonella, as well as members of the genera Pseudomonas, Streptomyces, and Staphylococcus. For expression in prokaryotic cells, for example, in *E. coli*, the polynucleotide molecule encoding GuxA polypeptide preferably includes an N-terminal methionine residue to facilitate expression of the recombinant polypeptide. The N-terminal Met may optionally be cleaved from the expressed polypeptide.

Expression vectors for use in prokaryotic hosts generally comprise one or more phenotypic selectable marker genes. Such genes encode, for example, a protein that confers antibiotic resistance or that supplies an auxotrophic requirement. A wide variety of such vectors are readily available from commercial sources. Examples include pSPORT vectors, pGEM vectors (Promega, Madison, Wis.), pPROEX vectors (LTI, Bethesda, Md.), Bluescript vectors (Stratagene), and pQE vectors (Qiagen).

GuxA can also be expressed in yeast host cells from genera including Saccharomyces, Pichia, and Kluveromyces. Preferred yeast hosts are *S. cerevisiae* and *P. pastoris*. Yeast vectors will often contain an origin of replication sequence from a 2T yeast plasmid, an autonomously replicating sequence (ARS), a promoter region, sequences for polyadenylation, sequences for transcription termination, and a selectable marker gene. Vectors replicable in both yeast and *E. coli* (termed shuttle vectors) may also be used. In addition to the above-mentioned features of yeast vectors, a shuttle vector will also include sequences for replication and selection in *E. coli*. Direct secretion of the target polypeptides expressed in yeast hosts may be accomplished by the inclusion of nucleotide sequence encoding the yeast I-factor leader sequence at the 5' end of the GuxA-encoding nucleotide sequence.

Insect host cell culture systems can also be used for the expression of GuxA polypeptides. The target polypeptides of the invention are preferably expressed using a baculovirus expression system, as described, for example, in the review by Luckow and Summers, 1988 *Bio/Technology* 6:47.

The choice of a suitable expression vector for expression of GuxA polypeptides of the invention will depend upon the host cell to be used. Examples of suitable expression vectors for *E. coli* include pET, pUC, and similar vectors as is known in the art. Preferred vectors for expression of the GuxA polypeptides include the shuttle plasmid pIJ702 for *Streptomyces lividans*, pGAPZalpha-A, B, C and pPICZalpha-A, B, C (Invitrogen) for *Pichia pastoris*, and pFE-1 and pFE-2 for filamentous fungi and similar vectors as is known in the art.

Modification of a GuxA polynucleotide molecule to facilitate insertion into a particular vector (for example, by modifying restriction sites), ease of use in a particular expression system or host (for example, using preferred host codons), and the like, are known and are contemplated for use in the invention. Genetic engineering methods for the production of GuxA polypeptides include the expression of the polynucleotide molecules in cell free expression systems, in cellular hosts, in tissues, and in animal models, according to known methods.

Compositions

The invention provides compositions containing a substantially purified GuxA polypeptide of the invention and an acceptable carrier. Such compositions are administered to biomass, for example, to degrade the cellulose in the biomass into simpler carbohydrate units and ultimately, to sugars. These released sugars from the cellulose are converted into ethanol by any number of different catalysts. Such compositions may also be included in detergents for removal, for example, of cellulose containing stains within fabrics, or compositions used in the pulp and paper industry, to address conditions associated with cellulose content. Compositions of the present invention can be used in stonewashing jeans such as is well known in the art. Compositions can be used in the biopolishing of cellulosic fabrics, such as cotton, linen, rayon and Lyocell.

The invention provides pharmaceutical compositions containing a substantially purified GuxA polypeptide of the invention and if necessary a pharmaceutically acceptable carrier. Such pharmaceutical compositions are administered to cells, tissues, or patients, for example, to aid in delivery or targeting of other pharmaceutical compositions. For example, GuxA polypeptides may be used where carbohydrate-mediated liposomal interactions are involved with target cells. Vyas SP et al. (2001), *J. Pharmacy & Pharmaceutical Sciences* May-Aug 4(2): 138–58.

The invention also provides reagents, compositions, and methods that are useful for analysis of GuxA activity and for the analysis of cellulose breakdown.

Compositions of the present invention may also include other known cellulases, and preferably, other known thermal tolerant cellulases for enhanced treatment of cellulose.

Antibodies

The polypeptides of the present invention, in whole or in part, may be used to raise polyclonal and monoclonal antibodies that are useful in purifying GuxA, or detecting GuxA polypeptide expression, as well as a reagent tool for characterizing the molecular actions of the GuxA polypeptide. Preferably, a peptide containing a unique epitope of the GuxA polypeptide is used in preparation of antibodies, using conventional techniques. Methods for the selection of peptide epitopes and production of antibodies are known. See, for example, Antibodies: *A Laboratory Manual*, Harlow and Land (eds.), 1988 Cold Spring Harbor Laboratory Press, Cold Spring Harbor, N.Y.; *Monoclonal Antibodies, Hybridomas*: A New Dimension in Biological Analyses, Kennet et al. (eds.), 1980 Plenum Press, New York.

Assays

Agents that modify, for example, increase or decrease, GuxA hydrolysis or degradation of cellulose can be identified, for example, by assay of GuxA cellulase activity and/or analysis of GuxA binding to a cellulose substrate. Incubation of cellulose in the presence of GuxA and in the presence or absence of a test agent and correlation of cellulase activity or cellulose binding permits screening of such agents. For example, cellulase activity and binding assays may be performed in a manner similar to those described in Irwin et al., *J. Bacteriology* 180(7): 1709–1714 (April 1998).

The GuxA stimulated activity is determined in the presence and absence of a test agent and then compared. A lower GuxA activated test activity in the presence of the test agent, than in the absence of the test agent, indicates that the test agent has decreased the activity of the GuxA. A higher GuxA activated test activity in the presence of the test agent than in the absence of the test agent indicates that the test agent has increased the activity of the GuxA. Stimulators and inhibitors of GuxA may be used to augment, inhibit, or modify GuxA mediated activity, and therefore may have potential industrial uses as well as potential use in the further elucidation of GuxA's molecular actions.

Therapeutic Applications

The GuxA polypeptides of the invention are effective in adding in delivery or targeting of other pharmaceutical compositions within a host. For example, GuxA polypeptides may be used where carbohydrate-mediated liposomal interactions are involved with target cells. Vyas SP et al. (2001), *J. Pharm Pharm Sci* May-Aug 4(2): 138–58.

GuxA polynucleotides and polypeptides, including vectors expressing GuxA, of the invention can be formulated as pharmaceutical compositions and administered to a host, preferably mammalian host, including a human patient, in a variety of forms adapted to the chosen route of administration. The compounds are preferably administered in combination with a pharmaceutically acceptable carrier, and may be combined with or conjugated to specific delivery agents, including targeting antibodies and/or cytokines.

GuxA can be administered by known techniques, such as orally, parentally (including subcutaneous injection, intravenous, intramuscular, intrastemal or infusion techniques), by inhalation spray, topically, by absorption through a mucous membrane, or rectally, in dosage unit formulations containing conventional non-toxic pharmaceutically acceptable carriers, adjuvants or vehicles. Pharmaceutical compositions of the invention can be in the form of suspensions or tablets suitable for oral administration, nasal sprays, creams, sterile injectable preparations, such as sterile injectable aqueous or oleagenous suspensions or suppositories.

For oral administration as a suspension, the compositions can be prepared according to techniques well-known in the art of pharmaceutical formulation. The compositions can contain microcrystalline cellulose for imparting bulk, alginic acid or sodium alginate as a suspending agent, methylcellulose as a viscosity enhancer, and sweeteners or flavoring agents. As immediate release tablets, the compositions can contain microcrystalline cellulose, starch, magnesium stearate and lactose or other excipients, binders, extenders, disintegrants, diluents and lubricants known in the art.

For administration by inhalation or aerosol, the compositions can be prepared according to techniques well-known in the art of pharmaceutical formulation. The compositions can be prepared as solutions in saline, using benzyl alcohol or other suitable preservatives, absorption promoters to enhance bioavailability, fluorocarbons or other solubilizing or dispersing agents known in the art.

For administration as injectable solutions or suspensions, the compositions can be formulated according to techniques well-known in the art, using suitable dispersing or wetting and suspending agents, such as sterile oils, including synthetic mono- or diglycerides, and fatty acids, including oleic acid.

For rectal administration as suppositories, the compositions can be prepared by mixing with a suitable non-irritating excipient, such as cocoa butter, synthetic glyceride esters or polyethylene glycols, which are solid at ambient temperatures, but liquefy or dissolve in the rectal cavity to release the drug.

Preferred administration routes include orally, parenterally, as well as intravenous, intramuscular or subcutaneous routes. More preferably, the compounds of the present invention are administered parenterally, i.e., intravenously or intraperitoneally, by infusion or injection.

Solutions or suspensions of the compounds can be prepared in water, isotonic saline (PBS) and optionally mixed with a nontoxic surfactant. Dispersions may also be prepared in glycerol, liquid polyethylene, glycols, DNA, vegetable oils, triacetin and mixtures thereof. Under ordinary conditions of storage and use, these preparations may contain a preservative to prevent the growth of microorganisms.

The pharmaceutical dosage form suitable for injection or infusion use can include sterile, aqueous solutions or dispersions or sterile powders comprising an active ingredient which are adapted for the extemporaneous preparation of sterile injectable or infusible solutions or dispersions. In all cases, the ultimate dosage form should be sterile, fluid and stable under the conditions of manufacture and storage. The liquid carrier or vehicle can be a solvent or liquid dispersion medium comprising, for example, water, ethanol, a polyol such as glycerol, propylene glycol, or liquid polyethylene glycols and the like, vegetable oils, nontoxic glyceryl esters, and suitable mixtures thereof. The proper fluidity can be maintained, for example, by the formation of liposomes, by the maintenance of the required particle size, in the case of dispersion, or by the use of nontoxic surfactants. The prevention of the action of microorganisms can be accomplished by various antibacterial and antifungal agents, for example, parabens, chlorobutanol, phenol, sorbic acid, thimerosal, and the like. In many cases, it will be desirable to include isotonic agents, for example, sugars, buffers, or sodium chloride. Prolonged absorption of the injectable compositions can be brought about by the inclusion in the composition of agents delaying absorption—for example, aluminum monosterate hydrogels and gelatin.

Sterile injectable solutions are prepared by incorporating the compounds in the required amount in the appropriate solvent with various other ingredients as enumerated above and, as required, followed by filter sterilization. In the case of sterile powders for the preparation of sterile injectable solutions, the preferred methods of preparation are vacuum drying and freeze-drying techniques, which yield a powder of the active ingredient plus any additional desired ingredient present in the previously sterile-filtered solutions.

Industrial Applications

The GuxA polypeptides of the invention are effective cellulases. In the methods of the invention, the cellulose degrading effects of GuxA are achieved by treating biomass at a ratio of about 1 to about 50 of GuxA:biomass. GuxA may be used under extreme conditions, for example, elevated temperatures and acidic pH. Treated biomass is degraded into simpler forms of carbohydrates, and in some cases glucose, which is then used in the formation of ethanol or other industrial chemicals, as is known in the art. Other methods are envisioned to be within the scope of the present invention, including methods for treating fabrics to remove cellulose-containing stains and other methods already discussed. GuxA polypeptides can be used in any known application currently utilizing a cellulase, all of which are within the scope of the present invention.

Having generally described the invention, the same will be more readily understood by reference to the following examples, which are provided by way of illustration and are not intended as limiting.

EXAMPLES

Example 1

Molecular Cloning of GuxA

Genomic DNA was isolated from *Acidothennus cellulolyticus* and purified by banding on cesium chloride gradients. Genomic DNA was partially digested with Sau 3A and separated on agarose gels. DNA fragments in the range of 9–20 kilobase pairs were isolated from the gels. This purified Sau 3A digested genomic DNA was ligated into the Bam H1 acceptor site of purified EMBL3 lambda phage arms (Clontech, San Diego, Calif.). Phage DNA was packaged according to the manufacturer's specifications and plated with *E. coli* LE392 in top agar which contained the soluble cellulose analog, carboxymethylcellulose (CMC). The plates were incubated overnight (12–24 hours) to allow transfection, bacterial growth, and plaque formation. Plates were stained with Congo Red followed by destaining with 1 M NaCl. Lambda plaques harboring endoglucanase clones showed up as unstained plaques on a red background.

Lambda clones which screened positive on CMC-Congo Red plates were purified by successive rounds of picking, plating and screening. Individual phage isolates were named SL-1, SL-2, SL-3 and SL-4. Subsequent subcloning efforts employed the SL-3 clone which contained an approximately 14.2 kb fragment of *A. cellulolyticus* genomic DNA.

Template DNA was constructed using a 9 kb BaniH1 fragment obtained from the 14.2 kb lambda clone SL3 prepared from *Acidothennus cellulolyticus* genomic DNA. The 9-kb BamHI fragment from SL3 was subcloned into pDR540 to generate a plasmid NREL501. NREL501 was first sequenced by the primer walking method as is known in the art. NREL501 was then subcloned into pUC19 using restriction enzymes PstI and EcoRI and transformed into *E. coli* XL1-blue (Stratagene, La Jolla, Calif.) for the production of template DNA for sequencing. Each subclone was sequenced from both forward and reverse directions. DNA for sequencing was prepared from an overnight growth in 500 mL LB broth using a megaprep DNA purification kit from Promega. The template DNA was PEG precipitated and suspended in de-ionized water and adjusted to a final concentration of 0.25 mg/mL. Custom primers were designed by reading upstream known sequence and selecting segments of an appropriate length to function, as is well known in the art. Primers for cycle sequencing were synthesized at the Macromolecular Resources facility located at Colorado State University in Fort Collins, Colo. Typically the sequencing primers were 26–30 nucleotides in length, but were sometimes longer or shorter to accommodate a melting temperature appropriate for cycle sequencing. The sequencing primers were diluted in de-ionized water, the concentration measured using UV absorbance at 260 nm, and then adjusted to a final concentration of 5 pmol/μL. Templates and sequencing primers were shipped to the Iowa State University DNA Sequencing facility at Ames, Iowa for sequencing using standard chemistries for cycle sequencing. In many cases, regions of the template that sequenced poorly using the standard protocols and dye terminators were repeated with the addition of 2 μL DMSO and by using nucleotides optimized for the sequencing of high GC content DNA. The high frequency of reoccurring small domains (ie, CBDs and linkers) with high sequence similarity caused initial difficulties in sequence assignments which were only resolved through extensive review of the data and repeat analyses.

Sequencing data from primer walking and subclones were assembled together to verify that all SL3 regions had been sequenced from both strands. An open reading frames (ORF) was found in the 9-kb BamHI fragment, C-terminal of E1 (U.S. Pat. No. 5,536,655), termed GuxA.

An ORF of about 3687 bp [SEQ ID NO: 2], including a stop codon, and deduced amino acid sequence [SEQ ID NO:1] are shown in Tables 1 and 2. The amino acid sequence predicted by SEQ ID NO: 1 was determined to have significant homology to known cellulases, as shown below in Example 2 and in Tables 3 and 4.

The amino acid sequence represents a novel member of the family of proteins with cellulase activity. Due to the source of isolation from the thermophilic organism Acidothermus, GuxA is a novel member of cellulases with properties including thermal tolerance. It is also known that thermal tolerant enzymes may have other properties (see definition above).

Example 2

GuxA includes a GH6 catalytic domain

Sequence alignments and comparisons of the amino acid sequences of the *Acidothermus cellulolyticus* GuxA first catalytic domain (aa 54 to 476), *Cellulomonas fimi* CBHA (beta-(1,4) exocellobiohydrolase) and *Thermobifida fusca* E3 (beta-(1,4) exocellulase) polypeptides were prepared, using the ClustalW program (Thompson J. D et al. (1994), Nucleic Acids Res. 22:4673–4680 from EMBL European Bioinformatics Institute website (http://www.ebi.ac.uk/).

An examination of the amino acid sequence alignment of the GH6 domains indicates that the amino acid sequence of the GuxA catalytic domain is homologous to the amino acid sequences of known GH6 family catalytic domains for *C. fimi* CBHA and *T. fusca* E3 (See Table 3). In Table 3, the notations are as follows: an asterisk "*" indicates identical or conserved residues in all sequences in the alignment; a colon ":" indicates conserved substitutions; a period "." indicates semi-conserved substitutions; and a hyphen "-" indicates a gap in the sequence. The amino acid sequence predicted for the GuxA GH6 domain is approximately 55% identical to the *C. fimi* CBHA GH6 domain and approximately 48% identical to the *T. fusca* E3 GH6 domain, indicating that the GuxA first catalytic domain is a member of the GH6 family (Henrissat et al. (1991), supra).

TABLE 3

Multiple amino acid sequence alignment of a GuxA first catalytic domain and polypeptides with Glycoside Hydrolase Family 6 catalytic domains.

```
Multialignment of related Glycoside Hydrolase Family 6 catalytic
domain
GH6_Ace: Acidothermus cellulolyticus GuxA catalytic domain GH6
CBHA_Cfi: Cellulomonas fimi CBHA (beta-1,4-exocellobiohydrolase).
GeneBank Acc. # AAC36898
E3_Tfu: Thermobifida fusca E3 (beta-1,4-exocellulase). GeneBank Acc.
# U18978

GH6_Ace   -ATHVDNPYAGATFFVNPYWAQEVQSEAANQTN-ATLAAKMRVVSTYSTAVWMDRIAAIN    (SEQ ID NO: 9)
CBHA_Cfi  APVHVDNPYAGAVQYVNPTWAASVNAAAGRQSADPALAAKMRTVAGQPTAVWMDRISAIT    (SEQ ID NO: 10)
E3_Tfu    PGGPTNPPTNPGEKVDNPFEGAKLYVNPVW-SAKAAAEPGGSAVANESTAVWLDRIGAIE    (SEQ ID NO: 11)
                 *         **   . .   ...:         *:  .****:***.**

GH6_Ace   GVN----GGPGLTTYLDAALSQQQGT-TPEVIEIVIYDLPGRDCAALASNGELPATAAGL
CBHA_Cfi  GNA----DGNGLKFHLDNAVAQQKAAGVPLVFNLVIYDLPGRDCFALASNGELPATDAGL
E3_Tfu    GNDSPTTGSMGLRDHLEEAVRQSGGD--PLTIQVVIYNLPGRDCAALASNGELGPDE--L
           *      .. **   :*: *: *. .   *  .:::***:****** ******* .     *

GH6_Ace   QTYETQYIDPIASILSN-PKYSSLRIVTIIEPDSLPNAVTNMSIQACATAVPYYEQ----
CBHA_Cfi  ARYKSEYIDPIADLLDN-PEYESIRIAATIEPDSLPNLTTNISEPACQQAAPYYRQ----
E3_Tfu    DRYKSEYIDPIADIMWDFADYENLRIVAIIEIDSLPNLVTNVGGNGGTELCAYMKQNGGY
            *::*******.::  :  ..*..:**.: ** ***** .**:. .    .* .*

GH6_Ace   --GIEYALTKLHAIPNVYIYMDAAHSGWLGWPNNASGYVQEVQKVLN-ASIGVNGIDGFV
CBHA_Cfi  --GVKYALDKLHAIPNVYNYIDIGHSGWLGWDSNAGPSATLFAEVAKSTTAGFASIDGFV
E3_Tfu    VNGVGYALRKLGEIPNVYNYIDAAHHGWIGWDSNFGPSVDIFYEAANASGSTVDYVHGFI
              *: *** **  ***** *:* .* **:**  .*    . .    . :. : :    . :.**:

GH6_Ace   TNTANYTPLKEPFMT-ATQQVGGQPVESANFYQWNPDIDEADYAVDLYSRLVAAGFPSSI
CBHA_Cfi  SDVANTTPLEEPLLSDSSLTINNTPIRSSKFYEWNFDFDEIDYTAHMHRLLVAAGFPSSI
E3_Tfu    SNTANYSATVEPYLD-VNGTVNGQLIRQSKWVDWNQYVDELSFVQDLRQALIAKGFRSDI
          ::.** :.  **  :   .  ...  :..::: :**  .** .:. .:   *:* ** *.*

GH6_Ace   GMLIDTLRNGWGGPNEPTGPSTATDVNTFVNQSKIDLRQHRGLWCNQNGAGLGQPPQASP
CBHA_Cfi  GMLVDTSRNGWGGPNRPTSITASTDVNAYVDANRVDRRVHRGAWCNPLGAGIGRFPEATP
E3_Tfu    GMLIDTSRNGWGGPNRPTGPSSSTDLNTYVDESRIDRRIHPGNWCNQAGAGLGERPTVNP
          ***:** ********.**. :::**:*:::*: .::*  *  *  *** ***:*. * ..*

GH6_Ace   TDFPNAHLDAYVWIKPPGESDGTSAASDPTTGKKSDPMCDPTYTTS--YGVLTN-ALPNS
CBHA_Cfi  SGYAASHLDAFVWIKPPGESDGASTDIPNDQGKRFDRMCDPTFVSPKLNNQLTG-ATPNA
E3_Tfu    ----APGVDAYVWVKPPGESDGASEEIPNDEGKGFDRMCDPTYQGNARNGNNPSGALPNA
             . :**:**:*********:*       ** * *****:      .  ... * **:

GH6_Ace   PIAGQWFPAQFDQLVANARPAV
CBHA_Cfi  PLAGQWFEEQFVTLVKNAYPVI
E3_Tfu    PISGHWFSAQFRELLANAYPPL
          *::*:**  **   *:  ** * :
```

Example 3

GuxA Includes a GH12 Catalytic Domain

Sequence alignments and comparisons of the amino acid sequences of the *Acidothermus cellulolyticus* GuxA second catalytic domain (aa 860 to 1090), *Streptomyces* sp. 11AG8 cellulase 12A (endoglucanase) and *Streptomyces lividans* cellulase B (endoglucanase) polypeptides were prepared, using the ClustalW program (EMBL; supra). An examination of the amino acid sequence alignment of the GH12 domains indicates that the amino acid sequence of the GuxA second catalytic domain is homologous to the amino acid sequences of known GH12 family catalytic domains for *Streptomyces* sp. cellulase 12A and *S. lividans* cellulase B (See Table 4). The amino acid sequence predicted for the GuxA GH6 domain is approximately 45% identical to the *Streptomyces* sp. cellulase 12A GH12 domain and approximately 42% identical to the *S. lividans* cellulase B GH12 domain, indicating that the GuxA second catalytic domain is a member of the GH12 family (Henrissat et al. (1991), supra).

TABLE 4

Multiple amino acid sequence alignment of a GuxA second catalytic
domain and polypeptides with Glycoside Hydrolase Family 12
catalytic domains.

Multialignment of related Glycoside Hydrolase Family 12 catalytic domain
GH12_Ace: *Acidothermus cellulolyticus* GuxA Hydrolase Family 12 catalytic domain
Cel12A_Ssp: *Streptomyces* sp. 11AG8 cellulase 12A(endoglucanase).
GeneBank Acc. # AAF91283.
CelB_Sli: *Streptomyces lividans* cellulase B (endoglucanase).
GeneBank Acc. # AAB71950

```
Cel12A_SSp    NQQICDRYGTTTIQD-RYVVQNNRWGTSATQCINV-TGNG-FEITQADGSVPTN          (SEQ ID NO: 12)
CelB_SLi      DTTICEPFGTTTIQG-RYVVQNNRWGSTAPQCVTA-TDTG-FRVTQADGSAPTN          (SEQ ID NO: 13)
GH12_ACe      CTPGPNQNGVTSVQGDEYRVQTNEWNSSAQQCLTINTATGAWTVSTANFSGGTG          (SEQ ID NO: 14)
              *.*::*. .* **.*.*.::* **:.   * .* : :: *: *  *.

Cel12A_SSp    GAPKSYPSVYDGCHYGNCAPR-TTLPMRISSIGSAPSSVSYRYTGNGVYNAAYDIWLDPT
CelB_SLi      GAPKSYPSVFNGCHYTNCSPG-TDLPVRLDTVSAAPSSISYGFVDGAVYNASYDIWLDPT
GH12_ACe      GAPATYPSIYKGCHWGNCTTKNVGMPIQISQIGSAVTSWSTTQVSSGAYDVAYDIWTNST
              *** :***::.***: **:.  . :*:::. :..:* :* *   .....*:.:**** :.*

Cel12A_SSp    PRTNG-VNRTEIMIWFNRVGPVQPIGSPVGT-AHVGGRSWEVWTGSNGSNDVISFLAPSA
CelB_SLi      ARTDG-VNQTEIMIWFNRVGPIQPIGSPVGT-ASVGGRTWEVWSGGNGSNDVLSFVAPSA
GH12_ACe      PTTTGQPNGTEIMIWLNSRGGVQPFGSQTATGVTVAGHTWNVWQGGQQTSWKIISYVLTPG
              . * * ******:*  * :**:** ..* . *.*::*:** * : * ..:*:: ...

Cel12A_SSp    ISSWS-FDVKDFVDQAVSHGLATPDWYLTSIQAGFEPWEGGTGLAVNSFSSAVN
CelB_SLi      ISGWS-FDVMDFVRATVARGLAENDWYLTSVQAGFEPWQNGAGLAVNSFSSTVE
GH12_ACe      ATSISNLDLKAIFADAAAARGSLNTSDYLLDVEAGFEIWQGGQGLGSNSFSVSVT
              :. * :*: :. :.::*  . ** .::**** *:.* **. **** :*
```

Example 4

Mixed Domain GH6, GH12, CBD II, CBD III Genes and Hybrid Polypeptides

From the putative locations of the domains in the GuxA cellulase sequence given above and in comparable cloned cellulase sequences from other species, one can separate individual domains and combine them with one or more domains from different sequences. The significant similarity between cellulase genes permit one by recombinant techniques to arrange one or more domains from the *Acidothermus cellulolyticus* GuxA cellulase gene with one or more domains from a cellulase gene from one or more other microorganisms. Other representative endoglucanase genes include *Bacillus polymyxa* beta-(1,4) endoglucanase (13aird et al, Journal of Bacteriology, 172: 1576–86 (1992)) and *Xanthomonas campestris* beta-(1,4)-endoglucanase A (Gough et al, Gene 89:53–59 (1990)). The result of the fusion of any two or more domains will, upon expression, be a hybrid polypeptide. Such hybrid polypeptides can have one or more catalytic or binding domains. For ease of manipulation, recombinant techniques may be employed such as the addition of restriction enzyme sites by site-specific mutagenesis. If one is not using one domain of a particular gene, any number of any type of change including complete deletion may be made in the unused domain for convenience of manipulation.

It is understood for purposes of this disclosure, that various changes and modifications may be made to the invention that are well within the scope of the invention. Numerous other changes may be made which will readily suggest themselves to those skilled in the art and which are encompassed in the spirit of the invention disclosed herein and as defined in the appended claims.

This specification contains numerous citations to references such as patents, patent applications, and publications. Each is hereby incorporated by reference for all purposes.

---

What is claimed is:

1. A composition comprising a thermostable GuxA poly peptide heterologously expressed in an organism other than *Acidothermus cellulolyticus*, said GuxA poly peptide comprising a first catalytic domain GH6, a second catalytic domain GH 12, a carbohydrate binding domain (CBD) type III, and a carbohydrate binding domain (CBD) type II.

2. The composition of claim 1 wherein the Gux A poly peptide is further defined as comprising a linker and a signal peptide.

3. The composition of claim 1 wherein the GH6 catalytic domain of the GuxA poly peptide is further defined as having a length of about 420 to about 425 amino acids.

4. The composition of claim 1, 2 or 3 wherein the GH12 catalytic domain of the GuxA poly peptide is further defined as having a length of about 225 to about 235 amino acids.

5. The composition of claim 1, 2, or 3 wherein the carbohydrate binding domain (CBD) type III of the GuxA poly peptide is further defined as having a length of about 145 to about 155 amino acids.

6. The composition of claim 1, 2, or 3 wherein the carbohydrate binding domain (CBD) type II of the GuxA poly peptide is further defined as having a length of about 95 amino acids to about 105 amino acids in length.

7. The composition of claim 3 wherein the GH6 catalytic domain is further defined as the sequence of SEQ ID NO: 4.

8. The composition of claim 4 wherein the GH12 catalytic domain is further defined as the sequence of SEQ ID NO: 7.

9. The composition of claim 5 wherein the carbohydrate binding domain (CBD) type III is further defined as the sequence of SEQ ID NO: 5.

10. The composition of claim 6 wherein the carbohydrate binding domain (CBD) type II is further defined as the sequence of SEQ ID NO:8.

11. The composition of claim 1 further defined as comprising a sequence of SEQ ID NO: 4, SEQ ID NO: 7, SEQ ID NO: 5 and SEQ ID NO: 8.

12. An isolated thermal tolerant GuxA poly peptide having a sequence of SEQ ID NO: 1.

13. The isolated thermal tolerant GuxA poly peptide of claim 12 further defined as having a sequence encoded by SEQ ID NO: 2.

14. An industrial mixture suitable for degrading cellulose, such mixture comprising the GuxA polypeptide of claim 1.

15. The industrial mixture of claim 14 further defined as comprising a detergent.

16. The composition of claim 1 wherein the GuxA polypeptide is further defined as comprising an amino acid sequence having at least 90% sequence identity to SEQ ID NO: 4.

17. The composition of claim 1 wherein the GuxA polypeptide is further defined as comprising an amino acid sequence having at least 90% sequence identity to SEQ IDNO: 7.

18. The composition of claim 1 wherein the GuxA polypeptide is further defined as comprising an amino acid sequence having at least 90% sequence identity to SEQ ID NO: 5.

19. The composition of claim 1 wherein the GuxA polypeptide is further defined as comprising an amino acid sequence having at least 90% sequence identity to SEQ ID NO: 8.

20. The composition of claim 1 wherein the GuxA polypeptide is further defined as comprising an amino acid sequence having at least 90% sequence identity to SEQ ID NO: 1.

21. The composition of claim 1 wherein the GuxA polypeptide is further defined as comprising an amino acid sequence encoded by a nucleic acid sequence having at least 90% identity to SEQ ID NO: 2.

22. The composition of claim 1 further comprising a heterologous peptide fused with said GuxA polypeptide.

23. The composition of claim 22 wherein the heterologous peptide comprises a peptide tag.

24. An isolated polypeptide molecule comprising:
a) a sequence of SEQ ID NO: 4;
b) a sequence of SEQ ID NO: 7;
c) a sequence of SEQ ID NO: 5;
d) a sequence of SEQ ID NO: 8;
e) a sequence of SEQ ID NO: 1; or
f) an amino acid sequence having about 90% sequence identity with the amino acid sequence of a), b), c), d), or e) and having at least one domain of glycosyl hydrolase family 6 and glycosyl hydrolase family 12.

25. A fusion protein comprising the mixture of claim 14 and a heterologous peptide.

26. The fusion protein of claim 25, wherein the heterologous peptide is a substrate targeting moiety.

27. The fusion protein of claim 25, wherein the heterologous peptide is a peptide tag.

28. The fusion protein of claim 27, wherein the peptide tag is 6-His, thioredoxin, hemaglutinin, GST, or OmpA signal sequence tag.

29. The fusion protein of claim 25, wherein the heterologous peptide is an agent that promotes polypeptide oligomerization.

30. The fusion protein of claim 25, wherein the heterologous peptide is a leucine zipper.

31. A cellulase-substrate complex comprising the isolated polypeptide molecule of claim 24 bound to cellulose.

32. A composition comprising the polypeptide molecule of claim 24 and a carrier.

33. A method for producing GuxA polypeptide, the method comprising: incubating a host cell genetically engineered to express the polypeptide molecule of claim 24.

34. The method of claim 33, further comprising the step of: isolating the polypeptide molecule from the incubated host cell.

35. The method of claim 34, wherein the host cell is a plant cell.

36. The method of claim 34, wherein the host cell is a bacterial cell.

37. The method of claim 34, wherein the host cell is genetically engineered to express a selectable marker.

38. The method of claim 34, wherein the host cell further comprises a polynucleotide molecule encoding one or more polypeptide molecules selected from the glycoside hydrolase family of proteins.

39. The method of claim 38, wherein the glycoside hydrolase is a thermostable glycoside hydrolase.

40. A method for assessing the carbohydrate hydrolysis activity of GuxA polypeptide comprising: analyzing a carbohydrate hydrolysis in the presence of GuxA polypeptide and a carbohydrate hydrolysis in the absence of GuxA polypeptide on a substrate; and comparing the carbohydrate hydrolysis in the presence of GuxA polypeptide with the carbohydrate hydrolysis in the absence of GuxA polypeptide.

41. A method for assessing the carbohydrate hydrolysis activity of GuxA polypeptide in the presence of an agent of interest comprising: analyzing a carbohydrate hydrolysis in the presence of GuxA polypeptide and a carbohydrate hydrolysis in the presence of GuxA polypeptide and the agent of interest on a substrate; and comparing the carbohydrate hydrolysis in the GuxA polypeptide treated substrate with the carbohydrate hydrolysis in the GuxA polypeptide treated substrate in the presence of the agent of interest.

42. The method of claim 41, wherein an increase in carbohydrate hydrolysis activity in the presence of the agent of interest demonstrates stimulation of GuxA polypeptide activity and wherein a decrease in carbohydrate hydrolysis activity demonstrates inhibition of GuxA polyp eptide activity.

43. The method of claim 40, wherein the carbohydrate is cellulose.

44. The method of claim 41 wherein the agent of interest is an antibody.

45. A method for hydrolyzing cellulose in a starting material, the method comprising: administering to the starting material an effective amount of a polypeptide molecule of claim 24.

46. The method of claim 45, further comprising administering a second polypeptide molecule selected from the glycoside hydrolase family of proteins.

47. A method for hydrolyzing cellulose in a starting material, the method comprising administering to the starting material an effective amount of a polypeptide molecule of claim 24, wherein the polypeptide molecule is thermostable.

48. The method of claim 45, wherein the starting material is agricultural biomass.

49. The method of claim 45, wherein the starting material is municipal solid waste.

50. The composition of claim 22 wherein the heterologous peptide further comprises a substrate targeting moiety.

51. A composition comprising a GuxA-derived peptide, said peptide comprising at least one catalytic domain selected from GH6 and GH 12 domains, and at least one carbohydrate binding domain selected from CBD type II and CBD type III domains.

52. The composition of claim 51 further comprising a heterologous peptide fused with said GuxA-derived peptide.

53. The composition of claim 52 wherein said heterologous peptide is a peptide tag.

54. The fusion protein of claim 52 wherein said heterologous peptide comprises a catalytic domain of a glycoside hydrolase other than GuxA.

55. The fusion protein of claim 52 wherein said heterologous peptide comprises a binding domain of a glycoside hydrolase other than GuxA.

56. The composition of claim 2, wherein the signal peptide is at least 60 percent identical to SEQ ID No. 3.

57. The composition of claim 2, wherein the signal peptide is derived from the signal peptide of other secretory proteins.

\* \* \* \* \*

SEQUENCE LISTING

```
<160> NUMBER OF SEQ ID NOS: 14

<210> SEQ ID NO 1
<211> LENGTH: 1228
<212> TYPE: PRT
<213> ORGANISM: Artificial Sequence
<220> FEATURE:
<223> OTHER INFORMATION: Description of Artificial Sequence: Segment of
      GuxA

<400> SEQUENCE: 1

Met Glu Arg Thr Gln Gln Ser Gly Arg Asn Cys Arg Tyr Gln Arg Gly
 1               5                  10                  15
```

-continued

```
Thr Thr Arg Met Pro Ala Ile Ser Lys Arg Leu Arg Ala Gly Val Leu
             20                  25                  30

Ala Gly Ala Val Ser Ile Ala Ala Ser Ile Val Pro Leu Ala Met Gln
         35                  40                  45

His Pro Ala Ile Ala Ala Thr His Val Asp Asn Pro Tyr Ala Gly Ala
         50                  55                  60

Thr Phe Phe Val Asn Pro Tyr Trp Ala Gln Glu Val Gln Ser Glu Ala
65                  70                  75                  80

Ala Asn Gln Thr Asn Ala Thr Leu Ala Ala Lys Met Arg Val Val Ser
                 85                  90                  95

Thr Tyr Ser Thr Ala Val Trp Met Asp Arg Ile Ala Ala Ile Asn Gly
            100                 105                 110

Val Asn Gly Gly Pro Gly Leu Thr Thr Tyr Leu Asp Ala Ala Leu Ser
            115                 120                 125

Gln Gln Gln Gly Thr Thr Pro Glu Val Ile Glu Val Ile Tyr Asp
        130                 135                 140

Leu Pro Gly Arg Asp Cys Ala Ala Leu Ala Ser Asn Gly Glu Leu Pro
145                 150                 155                 160

Ala Thr Ala Ala Gly Leu Gln Thr Tyr Glu Thr Gln Tyr Ile Asp Pro
                165                 170                 175

Ile Ala Ser Ile Leu Ser Asn Pro Lys Tyr Ser Ser Leu Arg Ile Val
            180                 185                 190

Thr Ile Ile Glu Pro Asp Ser Leu Pro Asn Ala Val Thr Asn Met Ser
        195                 200                 205

Ile Gln Ala Cys Ala Thr Ala Val Pro Tyr Tyr Glu Gln Gly Ile Glu
        210                 215                 220

Tyr Ala Leu Thr Lys Leu His Ala Ile Pro Asn Val Tyr Ile Tyr Met
225                 230                 235                 240

Asp Ala Ala His Ser Gly Trp Leu Gly Trp Pro Asn Asn Ala Ser Gly
                245                 250                 255

Tyr Val Gln Glu Val Gln Lys Val Leu Asn Ala Ser Ile Gly Val Asn
            260                 265                 270

Gly Ile Asp Gly Phe Val Thr Asn Thr Ala Asn Tyr Thr Pro Leu Lys
        275                 280                 285

Glu Pro Phe Met Thr Ala Thr Gln Gln Val Gly Gly Gln Pro Val Glu
        290                 295                 300

Ser Ala Asn Phe Tyr Gln Trp Asn Pro Asp Ile Asp Glu Ala Asp Tyr
305                 310                 315                 320

Ala Val Asp Leu Tyr Ser Arg Leu Val Ala Ala Gly Phe Pro Ser Ser
                325                 330                 335

Ile Gly Met Leu Ile Asp Thr Leu Arg Asn Gly Trp Gly Pro Asn
        340                 345                 350

Glu Pro Thr Gly Pro Ser Thr Ala Thr Asp Val Asn Thr Phe Val Asn
        355                 360                 365

Gln Ser Lys Ile Asp Leu Arg Gln His Arg Gly Leu Trp Cys Asn Gln
        370                 375                 380

Asn Gly Ala Gly Leu Gly Gln Pro Gln Ala Ser Pro Thr Asp Phe
385                 390                 395                 400

Pro Asn Ala His Leu Asp Ala Tyr Val Trp Ile Lys Pro Pro Gly Glu
                405                 410                 415

Ser Asp Gly Thr Ser Ala Ala Ser Asp Pro Thr Thr Gly Lys Lys Ser
            420                 425                 430
```

```
Asp Pro Met Cys Asp Pro Thr Tyr Thr Thr Ser Tyr Gly Val Leu Thr
            435                 440                 445

Asn Ala Leu Pro Asn Ser Pro Ile Ala Gly Gln Trp Phe Pro Ala Gln
        450                 455                 460

Phe Asp Gln Leu Val Ala Asn Ala Arg Pro Ala Val Pro Thr Ser Thr
465                 470                 475                 480

Ser Ser Ser Pro Pro Pro Pro Pro Ser Pro Ser Ala Ser Pro Ser
                485                 490                 495

Pro Ser Pro Ser Pro Ser Pro Ser Ser Ser Pro Ser Pro Ser Pro Ser
            500                 505                 510

Pro Ser Ser Ser Pro Ser Pro Ser Pro Ser Pro Ser Pro Ser
            515                 520                 525

Ser Ser Pro Ser Pro Ser Pro Ser Ser Ser Pro Ser Pro Ser Pro Ser
            530                 535                 540

Pro Ser Pro Ser Pro Ser Ser Ser Pro Ser Pro Ser Pro Ser Ser Ser
545                 550                 555                 560

Pro Ser Pro Ser Pro Ser Pro Ser Pro Ser Ser Ser Pro Ser
            565                 570                 575

Pro Ser Pro Thr Ser Ser Pro Val Ser Gly Leu Lys Val Gln Tyr
            580                 585                 590

Lys Asn Asn Asp Ser Ala Pro Gly Asp Asn Gln Ile Lys Pro Gly Leu
            595                 600                 605

Gln Leu Val Asn Thr Gly Ser Ser Ser Val Asp Leu Ser Thr Val Thr
            610                 615                 620

Val Arg Tyr Trp Phe Thr Arg Asp Gly Gly Ser Ser Thr Leu Val Tyr
625                 630                 635                 640

Asn Cys Asp Trp Ala Ala Met Gly Cys Gly Asn Ile Arg Ala Ser Phe
                645                 650                 655

Gly Ser Val Asn Pro Ala Thr Pro Thr Ala Asp Thr Tyr Leu Gln Leu
                660                 665                 670

Ser Phe Thr Gly Gly Thr Leu Ala Ala Gly Gly Ser Thr Gly Glu Ile
            675                 680                 685

Gln Asn Arg Val Asn Lys Ser Asp Trp Ser Asn Phe Thr Glu Thr Asn
            690                 695                 700

Asp Tyr Ser Tyr Gly Thr Asn Thr Thr Phe Gln Asp Trp Thr Lys Val
705                 710                 715                 720

Thr Val Tyr Val Asn Gly Val Leu Val Trp Gly Thr Glu Pro Ser Gly
                725                 730                 735

Thr Ser Pro Ser Pro Thr Pro Ser Pro Ser Pro Ser Pro Ser
            740                 745                 750

Pro Gly Gly Asp Val Thr Pro Ser Val Pro Thr Gly Leu Val Val
            755                 760                 765

Thr Gly Val Ser Gly Ser Ser Val Ser Leu Ala Trp Asn Ala Ser Thr
            770                 775                 780

Asp Asn Val Gly Val Ala His Tyr Asn Val Tyr Arg Asn Gly Val Leu
785                 790                 795                 800

Val Gly Gln Pro Thr Val Thr Ser Phe Thr Asp Thr Gly Leu Ala Ala
                805                 810                 815

Gly Thr Ala Tyr Thr Tyr Thr Val Ala Ala Val Asp Ala Ala Gly Asn
            820                 825                 830

Thr Ser Ala Pro Ser Thr Pro Val Thr Ala Thr Thr Ser Pro Ser
            835                 840                 845
```

```
Pro Ser Pro Thr Pro Thr Gly Thr Thr Val Thr Asp Cys Thr Pro Gly
    850                 855                 860

Pro Asn Gln Asn Gly Val Thr Ser Val Gln Gly Asp Glu Tyr Arg Val
865                 870                 875                 880

Gln Thr Asn Glu Trp Asn Ser Ser Ala Gln Gln Cys Leu Thr Ile Asn
            885                 890                 895

Thr Ala Thr Gly Ala Trp Thr Val Ser Thr Ala Asn Phe Ser Gly Gly
        900                 905                 910

Thr Gly Gly Ala Pro Ala Thr Tyr Pro Ser Ile Tyr Lys Gly Cys His
            915                 920                 925

Trp Gly Asn Cys Thr Thr Lys Asn Val Gly Met Pro Ile Gln Ile Ser
    930                 935                 940

Gln Ile Gly Ser Ala Val Thr Ser Trp Ser Thr Thr Gln Val Ser Ser
945                 950                 955                 960

Gly Ala Tyr Asp Val Ala Tyr Asp Ile Trp Thr Asn Ser Thr Pro Thr
            965                 970                 975

Thr Thr Gly Gln Pro Asn Gly Thr Glu Ile Met Ile Trp Leu Asn Ser
        980                 985                 990

Arg Gly Gly Val Gln Pro Phe Gly Ser Gln Thr Ala Thr Gly Val Thr
    995                 1000                1005

Val Ala Gly His Thr Trp Asn Val Trp Gln Gly Gln Gln Thr Ser Trp
1010                1015                1020

Lys Ile Ile Ser Tyr Val Leu Thr Pro Gly Ala Thr Ser Ile Ser Asn
1025                1030                1035                1040

Leu Asp Leu Lys Ala Ile Phe Ala Asp Ala Ala Ala Arg Gly Ser Leu
                1045                1050                1055

Asn Thr Ser Asp Tyr Leu Leu Asp Val Glu Ala Gly Phe Glu Ile Trp
            1060                1065                1070

Gln Gly Gly Gln Gly Leu Gly Ser Asn Ser Phe Ser Val Ser Val Thr
        1075                1080                1085

Ser Gly Thr Ser Ser Pro Thr Pro Ser Pro Ser Pro Thr Pro Thr Pro
    1090                1095                1100

Ser Pro Thr Pro Thr Pro Ser Pro Ser Pro Thr Pro Ser Pro Ser Pro
1105                1110                1115                1120

Thr Ser Ser Pro Ser Ser Ser Gly Val Ala Cys Arg Ala Thr Tyr Val
                1125                1130                1135

Val Asn Ser Asp Trp Gly Ser Gly Phe Thr Ala Thr Val Thr Val Thr
            1140                1145                1150

Asn Thr Gly Ser Arg Ala Thr Asn Gly Trp Thr Val Ala Trp Ser Phe
        1155                1160                1165

Gly Gly Asn Gln Thr Val Thr Asn Tyr Trp Asn Thr Ala Leu Thr Gln
    1170                1175                1180

Ser Gly Ala Ser Val Thr Ala Thr Asn Leu Ser Tyr Asn Asn Val Ile
1185                1190                1195                1200

Gln Pro Gly Gln Ser Thr Thr Phe Gly Phe Asn Gly Ser Tyr Ser Gly
                1205                1210                1215

Thr Asn Ala Ala Pro Thr Leu Ser Cys Thr Ala Ser
            1220                1225

<210> SEQ ID NO 2
<211> LENGTH: 3687
<212> TYPE: DNA
<213> ORGANISM: Artificial Sequence
<220> FEATURE:
<223> OTHER INFORMATION: Description of Artificial Sequence: Segment of
```

-continued

GuxA

<400> SEQUENCE: 2

| | | | | | |
|---|---|---|---|---|---|
| atggagcgaa | cccaacaatc | cggacggaac | tgcaggtacc | agagaggaac | gacacgaatg | 60 |
| cccgccatct | caaaacggct | gcgagccggc | gtcctcgccg | gggcggtgag | catcgcagcc | 120 |
| tccatcgtgc | cgctggcgat | gcagcatcct | gccatcgccg | cgacgcacgt | cgacaatccc | 180 |
| tatgcgggag | cgaccttctt | cgtcaacccg | tactgggcgc | aagaagtaca | gagcgaagcg | 240 |
| gcgaaccaga | ccaatgccac | tctcgcagcg | aaaatgcgcg | tcgtttccac | atattcgacg | 300 |
| gccgtctgga | tggaccgcat | cgctgcgatc | aacggcgtca | acggcggacc | cggcttgacg | 360 |
| acatatctgg | acgccgccct | ctcccagcag | cagggaacca | cccctgaagt | cattgagatt | 420 |
| gtcatctacg | atctgccggg | acgcgactgc | gcggcgctcg | cctccaacgg | cgaactgccc | 480 |
| gctacggcag | caggtttgca | gacctatgaa | acgcagtaca | tcgatccgat | tgcgagtatc | 540 |
| ctgagcaatc | cgaagtactc | cagcctgcgc | atcgtgacga | tcattgagcc | ggactcgctg | 600 |
| ccaaacgcgg | tcaccaatat | gagcattcaa | gcgtgtgcaa | cggcggtgcc | gtattacgag | 660 |
| caaggcatcg | agtacgcgct | cacgaaattg | acgccattc | cgaacgtgta | catctacatg | 720 |
| gacgccgccc | actccggctg | gcttgggtgg | cccaataatg | ccagcggata | cgtacaggaa | 780 |
| gtccagaagg | tcctcaacgc | gagcatcggg | gtcaacggca | tcgacggctt | cgtcaccaac | 840 |
| acggcgaatt | acacgccgtt | gaaggagccg | ttcatgaccg | ccacccagca | ggtcggcgga | 900 |
| cagccggtgg | agtcggcgaa | tttctaccag | tggaatcctg | acatcgacga | agccgactac | 960 |
| gcggttgact | tgtactcgcg | gctcgtcgcc | gctggctttc | aagcagcat | cggcatgctc | 1020 |
| atcgacacct | tacgcaacgg | ttggggtggt | ccgaacgaac | caacaggccc | gagcaccgcg | 1080 |
| accgatgtca | acaccttcgt | caaccagtcg | aagattgacc | ttcggcagca | ccgcggcctg | 1140 |
| tggtgcaacc | agaacggtgc | gggcctcggc | cagccgccgc | aggcaagccc | gacggacttc | 1200 |
| ccgaacgcgc | acctcgacgc | gtatgtctgg | atcaagccgc | cgggtgagtc | ggacggcaca | 1260 |
| agcgctgcga | gcgatccgac | aactggcaag | aagtcggacc | ccatgtgcga | cccgacgtac | 1320 |
| acgacgtcgt | acggggtact | gaccaacgcg | ttaccgaact | cccgatcgc | cggccagtgg | 1380 |
| ttcccggcgc | agtttgacca | gcttgtcgcg | aacgcacggc | cagcggtgcc | gacgtcgacc | 1440 |
| agctcgagcc | cgccgcctcc | gccgccgagt | ccgtcggctt | cgccgagtcc | gagcccgagt | 1500 |
| ccgagcccga | gcagctcgcc | atcgccgtcg | ccgtctccga | gctcgagccc | gtctccgtcg | 1560 |
| ccgagcccga | gtccgagccc | gagtagctcg | ccgtcgccgc | tccgagctc | gagccgtct | 1620 |
| ccgtcgccga | gcccgagtcc | gagcccgagt | agctcgccgt | cgccgtctcc | gagctcgagc | 1680 |
| ccgtctccgt | cgccgagccc | gagtccgagc | cgagtagct | cgccgtcgcc | gtctccgacg | 1740 |
| tcgtcgccgg | tgtcgggtgg | gctgaaggtg | cagtacaaga | caatgattc | ggcgccgggt | 1800 |
| gataaccaga | tcaaaccggg | tctccagttg | gtgaataccg | gtcgtcgtc | ggtggatttg | 1860 |
| tcgacggtga | cggtgcggta | ctggttcacc | cgggatggtg | gtcgtcgac | actggtgtac | 1920 |
| aactgtgact | gggcggcgat | ggggtgtggg | aatatccgcg | cctcgttcgg | ctcggtgaac | 1980 |
| ccggcgacgc | cgacggcgga | cacctacctg | cagttgtcgt | tcactggtgg | aacgttggcc | 2040 |
| gctggtgggt | cgacgggtga | gattcaaaac | cgggtgaata | agagtgactg | gtcgaatttc | 2100 |
| accgagacca | atgactactc | gtatgggacg | aacaccacct | tccaggactg | gacgaaggtg | 2160 |
| acggtgtacg | tcaacggcgt | gttggtgtgg | gggactgaac | cgtccggcac | cagccccagc | 2220 |
| cccacaccat | ccccgagccc | gagcccgagc | cgagcccgg | gtggggatgt | gacgccgccg | 2280 |

-continued

```
agtgtgccga ccggcttggt ggtgacgggg gtgagtgggt cgtcggtgtc gttggcgtgg    2340
aatgcgtcga cggataacgt gggggtggcg cattacaacg tgtaccgcaa cggggtgttg    2400
gtgggccagc cgacggtgac ctcgttcacc gacacgggtt tggccgcggg aaccgcgtac    2460
acctacacgg tggccgcggt ggacgctgcg ggtaacacct ccgcccatc caccccgtc     2520 accgccacca ccacgagtcc cagccccagc cccacgccga cggggaccac ggtcaccgac    2580
tgcacgcccg gtcctaacca gaatggtgtg accagcgtgc agggcgacga ataccgggtg    2640
cagaccaatg agtggaattc gtcggcccag cagtgcctca ccatcaatac cgcgaccggt    2700
gcctggacgg tgagcactgc gaacttcagc ggtgggaccg gcggtgcgcc cgcgacgtat    2760
ccgtcgatct acaagggctg ccactggggc aactgcacca cgaagaacgt cgggatgccg    2820
attcagatca gtcagattgg ttcggctgtg acgtcgtgga gtacgacgca ggtgtcgtcg    2880
ggcgcgtatg acgtggccta cgacatttgg acgaacagta ccccaacgac aaccggtcag    2940
ccaaacggta ccgaaatcat gatttggctg aattcgcgtg gtggggtgca gccgttcggg    3000
tcgcagacag cgacggggtgt gacggtcgct ggtcacacgt ggaatgtctg caggggtcag    3060
cagacctcgt ggaagattat ttcctacgtc ctgaccccg gtgcgacgtc gatcagtaat    3120
ctggatttga aggcgatttt cgcggacgcc gcggcacgcg ggtcgctcaa cacctccgat    3180
tacctgctcg acgttgaggc cgggtttgag atctggcaag gtggtcaggg cctgggcagc    3240
aactcgttca gcgtctccgt gacgagcggc acgtccagcc cgacaccgag cccgagcccg    3300
acgccgacac cgagcccgac gccgacaccg tctccgagcc cgaccccgtc gccgagtccg    3360
accagctcgc cgtcgtcgtc gggtgtggcg tgccgggcga cgtatgtggt gaatagtgat    3420
tggggttctg ggtttacggc gacggtgacg gtgacgaata ccgggagccg ggcgacgaac    3480
gggtggacgg tggcgtggtc gtttggtggg aatcagacgg tcacgaacta ctggaacact    3540
gcgttgaccc aatcaggtgc atcggtgacg gcgacgaacc tgagttacaa caacgtgatc    3600
caaccgggtc agtcgaccac cttcggattc aacggaagtt actcaggaac aaacgccgcg    3660
ccgacgctca gctgcacagc cagctga                                        3687
```

<210> SEQ ID NO 3
<211> LENGTH: 53
<212> TYPE: PRT
<213> ORGANISM: Artificial Sequence
<220> FEATURE:
<223> OTHER INFORMATION: Description of Artificial Sequence: Segment of
    GuxA

<400> SEQUENCE: 3

Met Glu Arg Thr Gln Gln Ser Gly Arg Asn Cys Arg Tyr Gln Arg Gly
 1               5                  10                  15

Thr Thr Arg Met Pro Ala Ile Ser Lys Arg Leu Arg Ala Gly Val Leu
            20                  25                  30

Ala Gly Ala Val Ser Ile Ala Ala Ser Ile Val Pro Leu Ala Met Gln
        35                  40                  45

His Pro Ala Ile Ala
    50

<210> SEQ ID NO 4
<211> LENGTH: 423
<212> TYPE: PRT
<213> ORGANISM: Artificial Sequence
<220> FEATURE:
<223> OTHER INFORMATION: Description of Artificial Sequence: Segment of GuxA

<400> SEQUENCE: 4

```
Ala Thr His Val Asp Asn Pro Tyr Ala Gly Ala Thr Phe Phe Val Asn
  1               5                  10                  15

Pro Tyr Trp Ala Gln Glu Val Gln Ser Glu Ala Ala Asn Gln Thr Asn
             20                  25                  30

Ala Thr Leu Ala Ala Lys Met Arg Val Val Ser Thr Tyr Ser Thr Ala
         35                  40                  45

Val Trp Met Asp Arg Ile Ala Ala Ile Asn Gly Val Asn Gly Gly Pro
 50                  55                  60

Gly Leu Thr Thr Tyr Leu Asp Ala Ala Leu Ser Gln Gln Gln Gly Thr
 65                  70                  75                  80

Thr Pro Glu Val Ile Glu Ile Val Ile Tyr Asp Leu Pro Gly Arg Asp
                     85                  90                  95

Cys Ala Ala Leu Ala Ser Asn Gly Glu Leu Pro Ala Thr Ala Ala Gly
             100                 105                 110

Leu Gln Thr Tyr Glu Thr Gln Tyr Ile Asp Pro Ile Ala Ser Ile Leu
         115                 120                 125

Ser Asn Pro Lys Tyr Ser Ser Leu Arg Ile Val Thr Ile Ile Glu Pro
130                 135                 140

Asp Ser Leu Pro Asn Ala Val Thr Asn Met Ser Ile Gln Ala Cys Ala
145                 150                 155                 160

Thr Ala Val Pro Tyr Tyr Glu Gln Gly Ile Glu Tyr Ala Leu Thr Lys
                 165                 170                 175

Leu His Ala Ile Pro Asn Val Tyr Ile Tyr Met Asp Ala Ala His Ser
             180                 185                 190

Gly Trp Leu Gly Trp Pro Asn Asn Ala Ser Gly Tyr Val Gln Glu Val
         195                 200                 205

Gln Lys Val Leu Asn Ala Ser Ile Gly Val Asn Gly Ile Asp Gly Phe
    210                 215                 220

Val Thr Asn Thr Ala Asn Tyr Thr Pro Leu Lys Glu Pro Phe Met Thr
225                 230                 235                 240

Ala Thr Gln Gln Val Gly Gly Gln Pro Val Glu Ser Ala Asn Phe Tyr
                 245                 250                 255

Gln Trp Asn Pro Asp Ile Asp Glu Ala Asp Tyr Ala Val Asp Leu Tyr
             260                 265                 270

Ser Arg Leu Val Ala Ala Gly Phe Pro Ser Ser Ile Gly Met Leu Ile
         275                 280                 285

Asp Thr Leu Arg Asn Gly Trp Gly Gly Pro Asn Glu Pro Thr Gly Pro
    290                 295                 300

Ser Thr Ala Thr Asp Val Asn Thr Phe Val Asn Gln Ser Lys Ile Asp
305                 310                 315                 320

Leu Arg Gln His Arg Gly Leu Trp Cys Asn Gln Asn Gly Ala Gly Leu
                 325                 330                 335

Gly Gln Pro Pro Gln Ala Ser Pro Thr Asp Phe Pro Asn Ala His Leu
             340                 345                 350

Asp Ala Tyr Val Trp Ile Lys Pro Pro Gly Glu Ser Asp Gly Thr Ser
         355                 360                 365

Ala Ala Ser Asp Pro Thr Thr Gly Lys Lys Ser Asp Pro Met Cys Asp
    370                 375                 380

Pro Thr Tyr Thr Thr Ser Tyr Gly Val Leu Thr Asn Ala Leu Pro Asn
385                 390                 395                 400
```

-continued

Ser Pro Ile Ala Gly Gln Trp Phe Pro Ala Gln Phe Asp Gln Leu Val
                405                 410                 415

Ala Asn Ala Arg Pro Ala Val
            420

<210> SEQ ID NO 5
<211> LENGTH: 150
<212> TYPE: PRT
<213> ORGANISM: Artificial Sequence
<220> FEATURE:
<223> OTHER INFORMATION: Description of Artificial Sequence: Segment of
      GuxA

<400> SEQUENCE: 5

Val Ser Gly Gly Leu Lys Val Gln Tyr Lys Asn Asn Asp Ser Ala Pro
  1               5                  10                  15

Gly Asp Asn Gln Ile Lys Pro Gly Leu Gln Leu Val Asn Thr Gly Ser
            20                  25                  30

Ser Ser Val Asp Leu Ser Thr Val Thr Val Arg Tyr Trp Phe Thr Arg
        35                  40                  45

Asp Gly Gly Ser Ser Thr Leu Val Tyr Asn Cys Asp Trp Ala Ala Met
    50                  55                  60

Gly Cys Gly Asn Ile Arg Ala Ser Phe Gly Ser Val Asn Pro Ala Thr
 65                  70                  75                  80

Pro Thr Ala Asp Thr Tyr Leu Gln Leu Ser Phe Thr Gly Gly Thr Leu
                85                  90                  95

Ala Ala Gly Gly Ser Thr Gly Glu Ile Gln Asn Arg Val Asn Lys Ser
            100                 105                 110

Asp Trp Ser Asn Phe Thr Glu Thr Asn Asp Tyr Ser Tyr Gly Thr Asn
        115                 120                 125

Thr Thr Phe Gln Asp Trp Thr Lys Val Thr Val Tyr Val Asn Gly Val
    130                 135                 140

Leu Val Trp Gly Thr Glu
145                 150

<210> SEQ ID NO 6
<211> LENGTH: 1043
<212> TYPE: PRT
<213> ORGANISM: Artificial Sequence
<220> FEATURE:
<223> OTHER INFORMATION: Description of Artificial Sequence: Segment of
      GuxA

<400> SEQUENCE: 6

Met Glu Arg Thr Gln Gln Ser Gly Arg Asn Cys Arg Tyr Gln Arg Gly
  1               5                  10                  15

Thr Thr Arg Met Pro Ala Ile Ser Lys Arg Leu Arg Ala Gly Val Leu
            20                  25                  30

Ala Gly Ala Val Ser Ile Ala Ala Ser Ile Val Pro Leu Ala Met Gln
        35                  40                  45

His Pro Ala Ile Ala Ala Thr His Val Asp Asn Pro Tyr Ala Gly Ala
    50                  55                  60

Thr Phe Phe Val Asn Pro Tyr Trp Ala Gln Glu Val Gln Ser Glu Ala
 65                  70                  75                  80

Ala Asn Gln Thr Asn Ala Thr Leu Ala Ala Lys Met Arg Val Val Ser
                85                  90                  95

Thr Tyr Ser Thr Ala Val Trp Met Asp Arg Ile Ala Ala Ile Asn Gly
            100                 105                 110

-continued

```
Val Asn Gly Gly Pro Gly Leu Thr Thr Tyr Leu Asp Ala Ala Leu Ser
            115                 120                 125

Gln Gln Gln Gly Thr Thr Pro Glu Val Ile Glu Ile Val Ile Tyr Asp
        130                 135                 140

Leu Pro Gly Arg Asp Cys Ala Ala Leu Ala Ser Asn Gly Glu Leu Pro
145                 150                 155                 160

Ala Thr Ala Ala Gly Leu Gln Thr Tyr Glu Thr Gln Tyr Ile Asp Pro
                165                 170                 175

Ile Ala Ser Ile Leu Ser Asn Pro Lys Tyr Ser Ser Leu Arg Ile Val
            180                 185                 190

Thr Ile Ile Glu Pro Asp Ser Leu Pro Asn Ala Val Thr Asn Met Ser
        195                 200                 205

Ile Gln Ala Cys Ala Thr Ala Val Pro Tyr Tyr Glu Gln Gly Ile Glu
    210                 215                 220

Tyr Ala Leu Thr Lys Leu His Ala Ile Pro Asn Val Tyr Ile Tyr Met
225                 230                 235                 240

Asp Ala Ala His Ser Gly Trp Leu Gly Trp Pro Asn Asn Ala Ser Gly
                245                 250                 255

Tyr Val Gln Glu Val Gln Lys Val Leu Asn Ala Ser Ile Gly Val Asn
            260                 265                 270

Gly Ile Asp Gly Phe Val Thr Asn Thr Ala Asn Tyr Thr Pro Leu Lys
        275                 280                 285

Glu Pro Phe Met Thr Ala Thr Gln Gln Val Gly Gly Gln Pro Val Glu
    290                 295                 300

Ser Ala Asn Phe Tyr Gln Trp Asn Pro Asp Ile Asp Glu Ala Asp Tyr
305                 310                 315                 320

Ala Val Asp Leu Tyr Ser Arg Leu Val Ala Ala Gly Phe Pro Ser Ser
                325                 330                 335

Ile Gly Met Leu Ile Asp Thr Leu Arg Asn Gly Trp Gly Gly Pro Asn
            340                 345                 350

Glu Pro Thr Gly Pro Ser Thr Ala Thr Asp Val Asn Thr Phe Val Asn
        355                 360                 365

Gln Ser Lys Ile Asp Leu Arg Gln His Arg Gly Leu Trp Cys Asn Gln
    370                 375                 380

Asn Gly Ala Gly Leu Gly Gln Pro Pro Gln Ala Ser Pro Thr Asp Phe
385                 390                 395                 400

Pro Asn Ala His Leu Asp Ala Tyr Val Trp Ile Lys Pro Pro Gly Glu
                405                 410                 415

Ser Asp Gly Thr Ser Ala Ala Ser Asp Pro Thr Thr Gly Lys Lys Ser
            420                 425                 430

Asp Pro Met Cys Asp Pro Thr Tyr Thr Thr Ser Tyr Gly Val Leu Thr
        435                 440                 445

Asn Ala Leu Pro Asn Ser Pro Ile Ala Gly Gln Trp Phe Pro Ala Gln
    450                 455                 460

Phe Asp Gln Leu Val Ala Asn Ala Arg Pro Ala Val Val Ser Gly Gly
465                 470                 475                 480

Leu Lys Val Gln Tyr Lys Asn Asn Asp Ser Ala Pro Gly Asp Asn Gln
                485                 490                 495

Ile Lys Pro Gly Leu Gln Leu Val Asn Thr Gly Ser Ser Ser Val Asp
            500                 505                 510

Leu Ser Thr Val Thr Val Arg Tyr Trp Phe Thr Arg Asp Gly Gly Ser
        515                 520                 525
```

-continued

```
Ser Thr Leu Val Tyr Asn Cys Asp Trp Ala Ala Met Gly Cys Gly Asn
        530                 535                 540

Ile Arg Ala Ser Phe Gly Ser Val Asn Pro Ala Thr Pro Thr Ala Asp
545                 550                 555                 560

Thr Tyr Leu Gln Leu Ser Phe Thr Gly Gly Thr Leu Ala Ala Gly Gly
                565                 570                 575

Ser Thr Gly Glu Ile Gln Asn Arg Val Asn Lys Ser Asp Trp Ser Asn
            580                 585                 590

Phe Thr Glu Thr Asn Asp Tyr Ser Tyr Gly Thr Asn Thr Thr Phe Gln
        595                 600                 605

Asp Trp Thr Lys Val Thr Val Tyr Val Asn Gly Val Leu Val Trp Gly
610                 615                 620

Thr Glu Asp Val Thr Pro Pro Ser Val Pro Thr Gly Leu Val Val Thr
625                 630                 635                 640

Gly Val Ser Gly Ser Ser Val Ser Leu Ala Trp Asn Ala Ser Thr Asp
                645                 650                 655

Asn Val Gly Val Ala His Tyr Asn Val Tyr Arg Asn Gly Val Leu Val
            660                 665                 670

Gly Gln Pro Thr Val Thr Ser Phe Thr Asp Thr Gly Leu Ala Ala Gly
        675                 680                 685

Thr Ala Tyr Thr Tyr Thr Val Ala Ala Val Asp Ala Ala Gly Asn Thr
690                 695                 700

Ser Ala Pro Ser Thr Pro Val Asp Cys Thr Pro Gly Pro Asn Gln Asn
705                 710                 715                 720

Gly Val Thr Ser Val Gln Asp Gly Glu Tyr Arg Val Gln Thr Asn Glu
                725                 730                 735

Trp Asn Ser Ser Ala Gln Gln Cys Leu Thr Ile Asn Thr Ala Thr Gly
            740                 745                 750

Ala Trp Thr Val Ser Thr Ala Asn Phe Ser Gly Gly Thr Gly Gly Ala
        755                 760                 765

Pro Ala Thr Tyr Pro Ser Ile Tyr Lys Gly Cys His Trp Gly Asn Cys
770                 775                 780

Thr Thr Lys Asn Val Gly Met Pro Ile Gln Ile Ser Gln Ile Gly Ser
785                 790                 795                 800

Ala Val Thr Ser Trp Ser Thr Thr Gln Val Ser Ser Gly Ala Tyr Asp
                805                 810                 815

Val Ala Tyr Asp Ile Trp Thr Asn Ser Thr Pro Thr Thr Thr Gly Gln
            820                 825                 830

Pro Asn Gly Thr Glu Ile Met Ile Trp Leu Asn Ser Arg Gly Gly Val
        835                 840                 845

Gln Pro Phe Gly Ser Gln Thr Ala Thr Gly Val Thr Val Ala Gly His
850                 855                 860

Thr Trp Asn Val Trp Gln Gly Gln Gln Thr Ser Trp Lys Ile Ile Ser
865                 870                 875                 880

Tyr Val Leu Thr Pro Gly Ala Thr Ser Ile Ser Asn Leu Asp Leu Lys
                885                 890                 895

Ala Ile Phe Ala Asp Ala Ala Ala Arg Gly Ser Leu Asn Thr Ser Asp
            900                 905                 910

Tyr Leu Leu Asp Val Glu Ala Gly Phe Glu Ile Trp Gln Gly Gly Gln
        915                 920                 925

Gly Leu Gly Ser Asn Ser Phe Ser Val Ser Val Thr Ser Gly Gly Val
930                 935                 940
```

```
Ala Cys Arg Ala Thr Tyr Val Val Asn Ser Asp Trp Gly Ser Gly Phe
945                 950                 955                 960

Thr Ala Thr Val Thr Val Asn Thr Gly Ser Arg Ala Thr Asn Gly
            965                 970                 975

Trp Thr Val Ala Trp Ser Phe Gly Gly Asn Gln Thr Val Thr Asn Tyr
                980                 985                 990

Trp Asn Thr Ala Leu Thr Gln Ser Gly Ala Ser Val Thr Ala Thr Asn
        995                 1000                1005

Leu Tyr Ser Asn Asn Val Ile Gln Pro Gly Gln Ser Thr Thr Phe Gly
    1010                1015                1020

Phe Asn Gly Ser Tyr Ser Gly Thr Asn Ala Ala Pro Thr Leu Ser Cys
1025                1030                1035                1040

Thr Ala Ser

<210> SEQ ID NO 7
<211> LENGTH: 231
<212> TYPE: PRT
<213> ORGANISM: Artificial Sequence
<220> FEATURE:
<223> OTHER INFORMATION: Description of Artificial Sequence: Segment of
      GuxA

<400> SEQUENCE: 7

Asp Cys Thr Pro Gly Pro Asn Gln Asn Gly Val Thr Ser Val Gln Asp
1               5                   10                  15

Gly Glu Tyr Arg Val Gln Thr Asn Glu Trp Asn Ser Ser Ala Gln Gln
            20                  25                  30

Cys Leu Thr Ile Asn Thr Ala Thr Gly Ala Trp Thr Val Ser Thr Ala
        35                  40                  45

Asn Phe Ser Gly Gly Thr Gly Gly Ala Pro Ala Thr Tyr Pro Ser Ile
    50                  55                  60

Tyr Lys Gly Cys His Trp Gly Asn Cys Thr Thr Lys Asn Val Gly Met
65                  70                  75                  80

Pro Ile Gln Ile Ser Gln Ile Gly Ser Ala Val Thr Ser Trp Ser Thr
                85                  90                  95

Thr Gln Val Ser Ser Gly Ala Tyr Asp Val Ala Tyr Asp Ile Trp Thr
            100                 105                 110

Asn Ser Thr Pro Thr Thr Gly Gln Pro Asn Gly Thr Glu Ile Met
        115                 120                 125

Ile Trp Leu Asn Ser Arg Gly Gly Val Gln Pro Phe Gly Ser Gln Thr
    130                 135                 140

Ala Thr Gly Val Thr Val Ala Gly His Thr Trp Asn Val Trp Gln Gly
145                 150                 155                 160

Gln Gln Thr Ser Trp Lys Ile Ile Ser Tyr Val Leu Thr Pro Gly Ala
                165                 170                 175

Thr Ser Ile Ser Asn Leu Asp Leu Lys Ala Ile Phe Ala Asp Ala Ala
            180                 185                 190

Ala Arg Gly Ser Leu Asn Thr Ser Asp Tyr Leu Leu Asp Val Glu Ala
        195                 200                 205

Gly Phe Glu Ile Trp Gln Gly Gly Gln Gly Leu Gly Ser Asn Ser Phe
    210                 215                 220

Ser Val Ser Val Thr Ser Gly
225                 230

<210> SEQ ID NO 8
<211> LENGTH: 101
```

<212> TYPE: PRT
<213> ORGANISM: Artificial Sequence
<220> FEATURE:
<223> OTHER INFORMATION: Description of Artificial Sequence: Segment of GuxA

<400> SEQUENCE: 8

```
Gly Val Ala Cys Arg Ala Thr Tyr Val Val Asn Ser Asp Trp Gly Ser
 1               5                  10                  15
Gly Phe Thr Ala Thr Val Thr Val Thr Asn Thr Gly Ser Arg Ala Thr
                20                  25                  30
Asn Gly Trp Thr Val Ala Trp Ser Phe Gly Gly Asn Gln Thr Val Thr
            35                  40                  45
Asn Tyr Trp Asn Thr Ala Leu Thr Gln Ser Gly Ala Ser Val Thr Ala
50                  55                  60
Thr Asn Leu Tyr Ser Asn Asn Val Ile Gln Pro Gly Gln Ser Thr Thr
65                  70                  75                  80
Phe Gly Phe Asn Gly Ser Tyr Ser Gly Thr Asn Ala Ala Pro Thr Leu
                85                  90                  95
Ser Cys Thr Ala Ser
            100
```

<210> SEQ ID NO 9
<211> LENGTH: 423
<212> TYPE: PRT
<213> ORGANISM: Acidothermus cellulolyticus

<400> SEQUENCE: 9

```
Ala Thr His Val Asp Asn Pro Tyr Ala Gly Ala Thr Phe Phe Val Asn
 1               5                  10                  15
Pro Tyr Trp Ala Gln Glu Val Gln Ser Glu Ala Ala Asn Gln Thr Asn
                20                  25                  30
Ala Thr Leu Ala Ala Lys Met Arg Val Val Ser Thr Tyr Ser Thr Ala
            35                  40                  45
Val Trp Met Asp Arg Ile Ala Ala Ile Asn Gly Val Asn Gly Gly Pro
50                  55                  60
Gly Leu Thr Thr Tyr Leu Asp Ala Ala Leu Ser Gln Gln Gln Gly Thr
65                  70                  75                  80
Thr Pro Glu Val Ile Glu Ile Val Ile Tyr Asp Leu Pro Gly Arg Asp
                85                  90                  95
Cys Ala Ala Leu Ala Ser Asn Gly Glu Leu Pro Ala Thr Ala Ala Gly
            100                 105                 110
Leu Gln Thr Tyr Glu Thr Gln Tyr Ile Asp Pro Ile Ala Ser Ile Leu
        115                 120                 125
Ser Asn Pro Lys Tyr Ser Ser Leu Arg Ile Val Thr Ile Ile Glu Pro
130                 135                 140
Asp Ser Leu Pro Asn Ala Val Thr Asn Met Ser Ile Gln Ala Cys Ala
145                 150                 155                 160
Thr Ala Val Pro Tyr Tyr Glu Gln Gly Ile Glu Tyr Ala Leu Thr Lys
                165                 170                 175
Leu His Ala Ile Pro Asn Val Tyr Ile Tyr Met Asp Ala Ala His Ser
            180                 185                 190
Gly Trp Leu Gly Trp Pro Asn Asn Ala Ser Gly Tyr Val Gln Glu Val
        195                 200                 205
Gln Lys Val Leu Asn Ala Ser Ile Gly Val Asn Gly Ile Asp Gly Phe
210                 215                 220
```

-continued

```
Val Thr Asn Thr Ala Asn Tyr Thr Pro Leu Lys Glu Pro Phe Met Thr
225                 230                 235                 240

Ala Thr Gln Gln Val Gly Gly Gln Pro Val Glu Ser Ala Asn Phe Tyr
            245                 250                 255

Gln Trp Asn Pro Asp Ile Asp Glu Ala Asp Tyr Ala Val Asp Leu Tyr
                260                 265                 270

Ser Arg Leu Val Ala Ala Gly Phe Pro Ser Ser Ile Gly Met Leu Ile
            275                 280                 285

Asp Thr Leu Arg Asn Gly Trp Gly Gly Pro Asn Glu Pro Thr Gly Pro
            290                 295                 300

Ser Thr Ala Thr Asp Val Asn Thr Phe Val Asn Gln Ser Lys Ile Asp
305                 310                 315                 320

Leu Arg Gln His Arg Gly Leu Trp Cys Asn Gln Asn Gly Ala Gly Leu
                325                 330                 335

Gly Gln Pro Pro Gln Ala Ser Pro Thr Asp Phe Pro Asn Ala His Leu
            340                 345                 350

Asp Ala Tyr Val Trp Ile Lys Pro Pro Gly Glu Ser Asp Gly Thr Ser
            355                 360                 365

Ala Ala Ser Asp Pro Thr Thr Gly Lys Lys Ser Asp Pro Met Cys Asp
370                 375                 380

Pro Thr Tyr Thr Thr Ser Tyr Gly Val Leu Thr Asn Ala Leu Pro Asn
385                 390                 395                 400

Ser Pro Ile Ala Gly Gln Trp Phe Pro Ala Gln Phe Asp Gln Leu Val
            405                 410                 415

Ala Asn Ala Arg Pro Ala Val
            420

<210> SEQ ID NO 10
<211> LENGTH: 430
<212> TYPE: PRT
<213> ORGANISM: Cellulomonas fimi

<400> SEQUENCE: 10

Ala Pro Val His Val Asp Asn Pro Tyr Ala Gly Ala Val Gln Tyr Val
1               5                   10                  15

Asn Pro Thr Trp Ala Ala Ser Val Asn Ala Ala Gly Arg Gln Ser
                20                  25                  30

Ala Asp Pro Ala Leu Ala Ala Lys Met Arg Thr Val Ala Gly Gln Pro
            35                  40                  45

Thr Ala Val Trp Met Asp Arg Ile Ser Ala Ile Thr Gly Asn Ala Asp
        50                  55                  60

Gly Asn Gly Leu Lys Phe His Leu Asp Asn Ala Val Ala Gln Gln Lys
65                  70                  75                  80

Ala Ala Gly Val Pro Leu Val Phe Asn Leu Val Ile Tyr Asp Leu Pro
                85                  90                  95

Gly Arg Asp Cys Phe Ala Leu Ala Ser Asn Gly Glu Leu Pro Ala Thr
                100                 105                 110

Asp Ala Gly Leu Ala Arg Tyr Lys Ser Glu Tyr Ile Asp Pro Ile Ala
            115                 120                 125

Asp Leu Leu Asp Asn Pro Glu Tyr Glu Ser Ile Arg Ile Ala Ala Thr
            130                 135                 140

Ile Glu Pro Asp Ser Leu Pro Asn Leu Thr Thr Asn Ile Ser Glu Pro
145                 150                 155                 160

Ala Cys Gln Gln Ala Ala Pro Tyr Tyr Arg Gln Gly Val Lys Tyr Ala
                165                 170                 175
```

```
Leu Asp Lys Leu His Ala Ile Pro Asn Val Tyr Asn Tyr Ile Asp Ile
            180                 185                 190

Gly His Ser Gly Trp Leu Gly Trp Asp Ser Asn Ala Gly Pro Ser Ala
            195                 200                 205

Thr Leu Phe Ala Glu Val Ala Lys Ser Thr Thr Ala Gly Phe Ala Ser
            210                 215                 220

Ile Asp Gly Phe Val Ser Asp Val Ala Asn Thr Thr Pro Leu Glu Glu
225                 230                 235                 240

Pro Leu Leu Ser Asp Ser Ser Leu Thr Ile Asn Asn Thr Pro Ile Arg
                245                 250                 255

Ser Ser Lys Phe Tyr Glu Trp Asn Phe Asp Phe Asp Glu Ile Asp Tyr
                260                 265                 270

Thr Ala His Met His Arg Leu Leu Val Ala Ala Gly Phe Pro Ser Ser
            275                 280                 285

Ile Gly Met Leu Val Asp Thr Ser Arg Asn Gly Trp Gly Gly Pro Asn
            290                 295                 300

Arg Pro Thr Ser Ile Thr Ala Ser Thr Asp Val Asn Ala Tyr Val Asp
305                 310                 315                 320

Ala Asn Arg Val Asp Arg Arg Val His Arg Gly Ala Trp Cys Asn Pro
                325                 330                 335

Leu Gly Ala Gly Ile Gly Arg Phe Pro Glu Ala Thr Pro Ser Gly Tyr
            340                 345                 350

Ala Ala Ser His Leu Asp Ala Phe Val Trp Ile Lys Pro Pro Gly Glu
            355                 360                 365

Ser Asp Gly Ala Ser Thr Asp Ile Pro Asn Asp Gln Gly Lys Arg Phe
            370                 375                 380

Asp Arg Met Cys Asp Pro Thr Phe Val Ser Pro Lys Leu Asn Asn Gln
385                 390                 395                 400

Leu Thr Gly Ala Thr Pro Asn Ala Pro Leu Ala Gly Gln Trp Phe Glu
            405                 410                 415

Glu Gln Phe Val Thr Leu Val Lys Asn Ala Tyr Pro Val Ile
            420                 425                 430

<210> SEQ ID NO 11
<211> LENGTH: 432
<212> TYPE: PRT
<213> ORGANISM: Thermobifida fusca

<400> SEQUENCE: 11

Pro Gly Gly Pro Thr Asn Pro Thr Asn Pro Gly Glu Lys Val Asp
1               5                   10                  15

Asn Pro Phe Glu Gly Ala Lys Leu Tyr Val Asn Pro Val Trp Ser Ala
                20                  25                  30

Lys Ala Ala Glu Pro Gly Gly Ser Ala Val Ala Asn Glu Ser Thr
            35                  40                  45

Ala Val Trp Leu Asp Arg Ile Gly Ala Ile Glu Gly Asn Asp Ser Pro
    50                  55                  60

Thr Thr Gly Ser Met Gly Leu Arg Asp His Leu Glu Glu Ala Val Arg
65                  70                  75                  80

Gln Ser Gly Gly Asp Pro Leu Thr Ile Gln Val Val Ile Tyr Asn Leu
                85                  90                  95

Pro Gly Arg Asp Cys Ala Ala Leu Ala Ser Asn Gly Glu Leu Gly Pro
            100                 105                 110
```

```
Asp Glu Leu Asp Arg Tyr Lys Ser Glu Tyr Ile Asp Pro Ile Ala Asp
            115                 120                 125

Ile Met Trp Asp Phe Ala Asp Tyr Glu Asn Leu Arg Ile Val Ala Ile
        130                 135                 140

Ile Glu Ile Asp Ser Leu Pro Asn Leu Val Thr Asn Val Gly Gly Asn
145                 150                 155                 160

Gly Gly Thr Glu Leu Cys Ala Tyr Met Lys Gln Asn Gly Gly Tyr Val
                165                 170                 175

Asn Gly Val Gly Tyr Ala Leu Arg Lys Leu Gly Glu Ile Pro Asn Val
            180                 185                 190

Tyr Asn Tyr Ile Asp Ala Ala His His Gly Trp Ile Gly Trp Asp Ser
        195                 200                 205

Asn Phe Gly Pro Ser Val Asp Ile Phe Tyr Glu Ala Ala Asn Ala Ser
        210                 215                 220

Gly Ser Thr Val Asp Tyr Val His Gly Phe Ile Ser Asn Thr Ala Asn
225                 230                 235                 240

Tyr Ser Ala Thr Val Glu Pro Tyr Leu Asp Val Asn Gly Thr Val Asn
                245                 250                 255

Gly Gln Leu Ile Arg Gln Ser Lys Trp Val Asp Trp Asn Gln Tyr Val
            260                 265                 270

Asp Glu Leu Ser Phe Val Gln Asp Leu Arg Gln Ala Leu Ile Ala Lys
        275                 280                 285

Gly Phe Arg Ser Asp Ile Gly Met Leu Ile Asp Thr Ser Arg Asn Gly
        290                 295                 300

Trp Gly Gly Pro Asn Arg Pro Thr Gly Pro Ser Ser Thr Asp Leu
305                 310                 315                 320

Asn Thr Tyr Val Asp Glu Ser Arg Ile Asp Arg Ile His Pro Gly
                325                 330                 335

Asn Trp Cys Asn Gln Ala Gly Ala Gly Leu Gly Glu Arg Pro Thr Val
            340                 345                 350

Asn Pro Ala Pro Gly Val Asp Ala Tyr Val Trp Val Lys Pro Pro Gly
        355                 360                 365

Glu Ser Asp Gly Ala Ser Glu Ile Pro Asn Asp Glu Gly Lys Gly
        370                 375                 380

Phe Asp Arg Met Cys Asp Pro Thr Tyr Gln Gly Asn Ala Arg Asn Gly
385                 390                 395                 400

Asn Asn Pro Ser Gly Ala Leu Pro Asn Ala Pro Ile Ser Gly His Trp
                405                 410                 415

Phe Ser Ala Gln Phe Arg Glu Leu Leu Ala Asn Ala Tyr Pro Pro Leu
            420                 425                 430

<210> SEQ ID NO 12
<211> LENGTH: 221
<212> TYPE: PRT
<213> ORGANISM: Acidothermus cellulolyticus

<400> SEQUENCE: 12

Asn Gln Gln Ile Cys Asp Arg Tyr Gly Thr Thr Thr Ile Gln Asp Arg
1               5                   10                  15

Tyr Val Val Gln Asn Asn Arg Trp Gly Thr Ser Ala Thr Gln Cys Ile
                20                  25                  30

Asn Val Thr Gly Asn Gly Phe Glu Ile Thr Gln Ala Asp Gly Ser Val
            35                  40                  45
```

```
Pro Thr Asn Gly Ala Pro Lys Ser Tyr Pro Ser Val Tyr Asp Gly Cys
         50                  55                  60

His Tyr Gly Asn Cys Ala Pro Arg Thr Thr Leu Pro Met Arg Ile Ser
 65                  70                  75                  80

Ser Ile Gly Ser Ala Pro Ser Ser Val Ser Tyr Arg Tyr Thr Gly Asn
                 85                  90                  95

Gly Val Tyr Asn Ala Ala Tyr Asp Ile Trp Leu Asp Pro Thr Pro Arg
             100                 105                 110

Thr Asn Gly Val Asn Arg Thr Glu Ile Met Ile Trp Phe Asn Arg Val
         115                 120                 125

Gly Pro Val Gln Pro Ile Gly Ser Pro Val Gly Thr Ala His Val Gly
 130                 135                 140

Gly Arg Ser Trp Glu Val Trp Thr Gly Ser Asn Gly Ser Asn Asp Val
145                 150                 155                 160

Ile Ser Phe Leu Ala Pro Ser Ala Ile Ser Ser Trp Ser Phe Asp Val
                 165                 170                 175

Lys Asp Phe Val Asp Gln Ala Val Ser His Gly Leu Ala Thr Pro Asp
             180                 185                 190

Trp Tyr Leu Thr Ser Ile Gln Ala Gly Phe Glu Pro Trp Glu Gly Gly
         195                 200                 205

Thr Gly Leu Ala Val Asn Ser Phe Ser Ser Ala Val Asn
 210                 215                 220

<210> SEQ ID NO 13
<211> LENGTH: 221
<212> TYPE: PRT
<213> ORGANISM: Streptomyces sp.

<400> SEQUENCE: 13

Asp Thr Thr Ile Cys Glu Pro Phe Gly Thr Thr Thr Ile Gln Gly Arg
  1               5                  10                  15

Tyr Val Val Gln Asn Asn Arg Trp Gly Ser Thr Ala Pro Gln Cys Val
             20                  25                  30

Thr Ala Thr Asp Thr Gly Phe Arg Val Thr Gln Ala Asp Gly Ser Ala
         35                  40                  45

Pro Thr Asn Gly Ala Pro Lys Ser Tyr Pro Ser Val Phe Asn Gly Cys
 50                  55                  60

His Tyr Thr Asn Cys Ser Pro Gly Thr Asp Leu Pro Val Arg Leu Asp
 65                  70                  75                  80

Thr Val Ser Ala Ala Pro Ser Ser Ile Ser Tyr Gly Phe Val Asp Gly
                 85                  90                  95

Ala Val Tyr Asn Ala Ser Tyr Asp Ile Trp Leu Asp Pro Thr Ala Arg
             100                 105                 110

Thr Asp Gly Val Asn Gln Thr Glu Ile Met Ile Trp Phe Asn Arg Val
         115                 120                 125

Gly Pro Ile Gln Pro Ile Gly Ser Pro Val Gly Thr Ala Ser Val Gly
 130                 135                 140

Gly Arg Thr Trp Glu Val Trp Ser Gly Gly Asn Gly Ser Asn Asp Val
145                 150                 155                 160

Leu Ser Phe Val Ala Pro Ser Ala Ile Ser Gly Trp Ser Phe Asp Val
                 165                 170                 175

Met Asp Phe Val Arg Ala Thr Val Ala Arg Gly Leu Ala Glu Asn Asp
             180                 185                 190
```

```
Trp Tyr Leu Thr Ser Val Gln Ala Gly Phe Glu Pro Trp Gln Asn Gly
        195                 200                 205

Ala Gly Leu Ala Val Asn Ser Phe Ser Ser Thr Val Glu
    210                 215                 220

<210> SEQ ID NO 14
<211> LENGTH: 228
<212> TYPE: PRT
<213> ORGANISM: Streptomyces lividans

<400> SEQUENCE: 14

Cys Thr Pro Gly Pro Asn Gln Asn Gly Val Thr Ser Val Gln Gly Asp
  1               5                  10                  15

Glu Tyr Arg Val Gln Thr Asn Glu Trp Asn Ser Ser Ala Gln Gln Cys
                 20                  25                  30

Leu Thr Ile Asn Thr Ala Thr Gly Ala Trp Thr Val Ser Thr Ala Asn
             35                  40                  45

Phe Ser Gly Gly Thr Gly Gly Ala Pro Ala Thr Tyr Pro Ser Ile Tyr
     50                  55                  60

Lys Gly Cys His Trp Gly Asn Cys Thr Thr Lys Asn Val Gly Met Pro
 65                  70                  75                  80

Ile Gln Ile Ser Gln Ile Gly Ser Ala Val Thr Ser Trp Ser Thr Thr
                 85                  90                  95

Gln Val Ser Ser Gly Ala Tyr Asp Val Ala Tyr Asp Ile Trp Thr Asn
                100                 105                 110

Ser Thr Pro Thr Thr Thr Gly Gln Pro Asn Gly Thr Glu Ile Met Ile
            115                 120                 125

Trp Leu Asn Ser Arg Gly Gly Val Gln Pro Phe Gly Ser Gln Thr Ala
    130                 135                 140

Thr Gly Val Thr Val Ala Gly His Thr Trp Asn Val Trp Gln Gly Gln
145                 150                 155                 160

Gln Thr Ser Trp Lys Ile Ile Ser Tyr Val Leu Thr Pro Gly Ala Thr
                165                 170                 175

Ser Ile Ser Asn Leu Asp Leu Lys Ala Ile Phe Ala Asp Ala Ala Ala
            180                 185                 190

Arg Gly Ser Leu Asn Thr Ser Asp Tyr Leu Leu Asp Val Glu Ala Gly
            195                 200                 205

Phe Glu Ile Trp Gln Gly Gly Gln Gly Leu Gly Ser Asn Ser Phe Ser
    210                 215                 220

Val Ser Val Thr
225
```